(12) United States Patent
Chey et al.

(10) Patent No.: US 9,743,857 B2
(45) Date of Patent: Aug. 29, 2017

(54) DIGITAL MANOMETRY FINGER-MOUNTABLE SENSOR DEVICE

(71) Applicants: THE REGENTS OF THE UNIVERSITY OF MICHIGAN, Ann Arbor, MI (US); THE REGENTS OF THE UNIVERSITY OF CALIFORNIA, Oakland, CA (US); THE UNITED STATES OF AMERICA REPRESENTED BY THE DEPARTMENT OF VETERANS AFFAIRS, Washington, DC (US)

(72) Inventors: William D. Chey, Ann Arbor, MI (US); James A. Ashton-Miller, Ann Arbor, MI (US); Brennan M. R. Spiegel, Los Angeles (CA)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1041 days.

(21) Appl. No.: 13/714,728

(22) Filed: Dec. 14, 2012

(65) Prior Publication Data
US 2013/0158365 A1    Jun. 20, 2013

Related U.S. Application Data

(60) Provisional application No. 61/576,779, filed on Dec. 16, 2011.

(51) Int. Cl.
*A61B 8/00* (2006.01)
*A61B 5/00* (2006.01)
(Continued)

(52) U.S. Cl.
CPC ........ *A61B 5/04884* (2013.01); *A61B 5/1076* (2013.01); *A61B 5/11* (2013.01);
(Continued)

(58) Field of Classification Search
CPC ..... A61B 5/04884; A61B 5/11; A61B 5/1076; A61B 5/14503; A61B 8/4444; A61B 5/227
(Continued)

(56) References Cited

U.S. PATENT DOCUMENTS 4,765,343 A * 8/1988 Brenman ............. A61B 5/0404
600/384
6,391,869 B1   5/2002 Parks et al.
(Continued)

FOREIGN PATENT DOCUMENTS

WO   WO-2006/002313   1/2006
WO   WO-2008/131557   11/2008

OTHER PUBLICATIONS

Berek & Novak's Gynecology 14th Edition, Jonathan S. Berek Editor, <http://www.epubbud.com/read.php?g=XWL9CAZ3&tocp=24>, retrived from the internet on Apr. 24, 2013.
(Continued)

*Primary Examiner* — Max Hindenburg
*Assistant Examiner* — Jonathan M Foreman
(74) *Attorney, Agent, or Firm* — Marshall, Gerstein & Borun LLP

(57) ABSTRACT

A probe system includes a finger-mountable housing having a distal end and a proximal receptacle end. The proximal receptacle end defines an opening to receive a finger. The probe system also includes a probe assembly disposed on or within the finger-mountable housing and having at least a first sensor. The first sensor is positioned to measure a physical characteristic of a first tissue when the finger-mountable housing and probe assembly are inserted in a rectum of the patient.

29 Claims, 20 Drawing Sheets

(51) Int. Cl.
*A61B 5/0488* (2006.01)
*A61B 5/22* (2006.01)
*A61B 5/107* (2006.01)
*A61B 5/11* (2006.01)
*A61B 5/145* (2006.01)

(52) U.S. Cl.
CPC .......... *A61B 5/14503* (2013.01); *A61B 5/227* (2013.01); *A61B 5/6806* (2013.01); *A61B 5/6826* (2013.01); *A61B 8/4444* (2013.01)

(58) Field of Classification Search
USPC ................................ 600/546, 561, 593, 595
See application file for complete search history.

(56) References Cited

U.S. PATENT DOCUMENTS

| | | | |
|---|---|---|---|
| 6,395,736 B1 | 5/2002 | Parks et al. | |
| 6,567,990 B1* | 5/2003 | Spitznagle | A61B 5/0492 2/160 |
| 6,625,495 B1 | 9/2003 | Alon et al. | |
| 6,627,632 B2 | 9/2003 | Parks et al. | |
| 6,741,895 B1* | 5/2004 | Gafni | A61B 5/4337 600/38 |
| 2002/0055761 A1 | 5/2002 | Mann et al. | |
| 2004/0015094 A1* | 1/2004 | Manabe | A61B 5/0492 600/546 |
| 2004/0054392 A1 | 3/2004 | Dijkman | |
| 2007/0118108 A1 | 5/2007 | Croft | |
| 2007/0129771 A1 | 6/2007 | Kurtz et al. | |
| 2007/0293792 A1* | 12/2007 | Sliwa | A61B 5/11 600/587 |
| 2009/0069721 A1* | 3/2009 | Kellett | A61B 5/1076 600/587 |
| 2009/0192346 A1 | 7/2009 | Rosenblatt | |
| 2010/0076254 A1 | 3/2010 | Jimenez et al. | |
| 2010/0152529 A1 | 6/2010 | Shalon et al. | |
| 2010/0256461 A1* | 10/2010 | Mohamedali | A61B 5/0086 600/301 |
| 2013/0150749 A1* | 6/2013 | McLean | A61B 5/04882 600/546 |

OTHER PUBLICATIONS

Invitation to Pay Additional Fees and, Where Applicable, Protest Fee in PCT Application No. PCT/US2012/069680, dated Apr. 5, 2013, 4 pages.
International Preliminary Report on Patentability in Application No. PCT/US2012/069680 dated Jun. 17, 2014.
Broman et al., A note on the noninvasive estimation of muscle fiber conduction velocity, IEEE Transactions on Bio-Medical Engineering, 32(5):341-4 (1985).
Cescon et al., Detection of individual motor units of the puborectalis muscle by non-invasive EMG electrode arrays, J. Electromyography and Kinesiology, 18(3):382-9 (2008).
Dall et al., The impact of improved colorectal cancer screening rates on adequacy rates of future supply of gastroenterologists, prepared for Olympus America Inc. (Jan. 7, 2009).
Dantec™ Neurodiagnostics Accessories Catalog, Natus Medial Incorporated (2010).
GE Industrial, NovaSensor 3F Medical Pressure Silicon Die, GE Sensing (2006).
Johanson et al., Chronic constipation: a survey of the patient perspective, Alimentary Pharmacology Therapeutics, 25(5):599-608 (2007).
Kiff et al., Slowed conduction in the pudendal nerves in idiopathic faecal incontinence, Br. J. Surg., 71:614-6 (1984).
Lefaucheur et al., Pudendal nerve terminal motor latency: age effects and technical considerations, Clin. Neurophysiology, 112:472-6 (2001).
Lembo et al., Chronic constipation, N. Engl. J. Med., 349(14):1360-8 (2003).
MacDonald et al., Relationship between intrabdominal and intrarectal pressure in the proctometrogram, Br. J. Surg., 80(8):1070 (1993).
Martin et al., Direct medical costs of constipation in the United States, Managed Care Interface, 19(12):43-9 (2006).
Papagrigoriadis, Incontinence, Bowel Health, retrieved from the Internet on Aug. 10, 2010, from <http://www.bowel-health.com/Incontinence.html>.
Rao et al., Clinical utility of colonic and anorectal manometry in chronic constipation, J. Clin. Gastroenterol., 44:597-609 (2010).
Rao et al., Randomized controlled trial of biofeedback, sham feedback, and standard therapy for dyssynergic defecation, Clinical Gastroenterology and Hepatology, 5(3):331-8 (2007).
Rao, Dyssynergic defecation and biofeedback therapy, Gastroenterology Clinics of North America, 37(3):569-86, viii (2008).
Rodgers et al., Disposable pudendal nerve stimulator: evaluation of the standard instrument and new device, Gut, 29:1131-3 (1988).
Schiller et al., An internet-based survey of the prevalence and symptom spectrum of chronic constipation, Am. J. Gastroenterol., 99:S234 (2004).
Vugt et al., A convenient method to reduce crosstalk in surface EMG, Clin. Neurophysiol., 112:583-92 (2001).
Search Report and Written Opinion in International Application No. PCT/US2012/069680 dated Jun. 13, 2013.
Office Action in EP Application No. 12818704.4 dated Dec. 20, 2016, 4 pages.

* cited by examiner

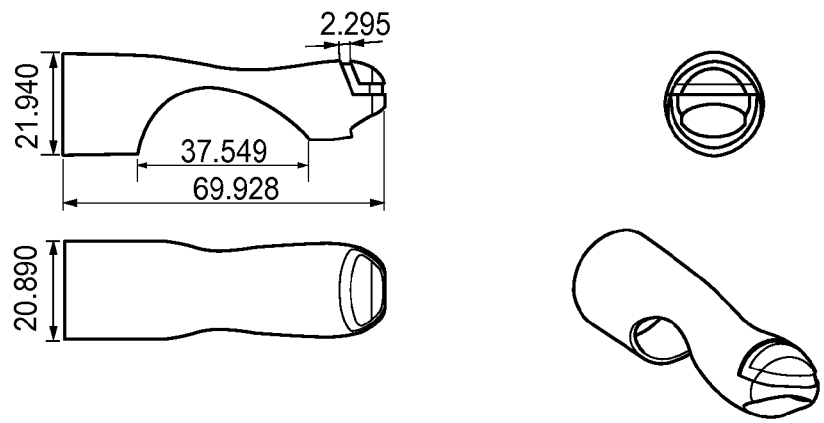
Detailed schematic of silicone inner layer.
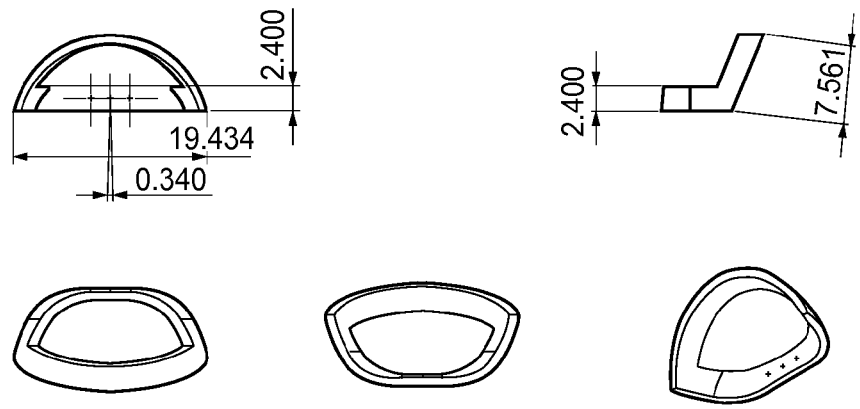
Detailed schematic of high density polyethylene supports.
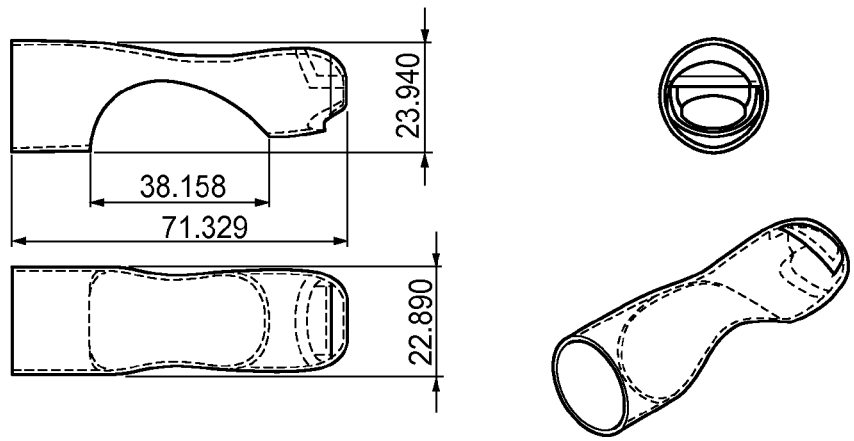
Detailed schematic of the silicone outer layer.
** all dimensions are given in millimeters.
Figure 4

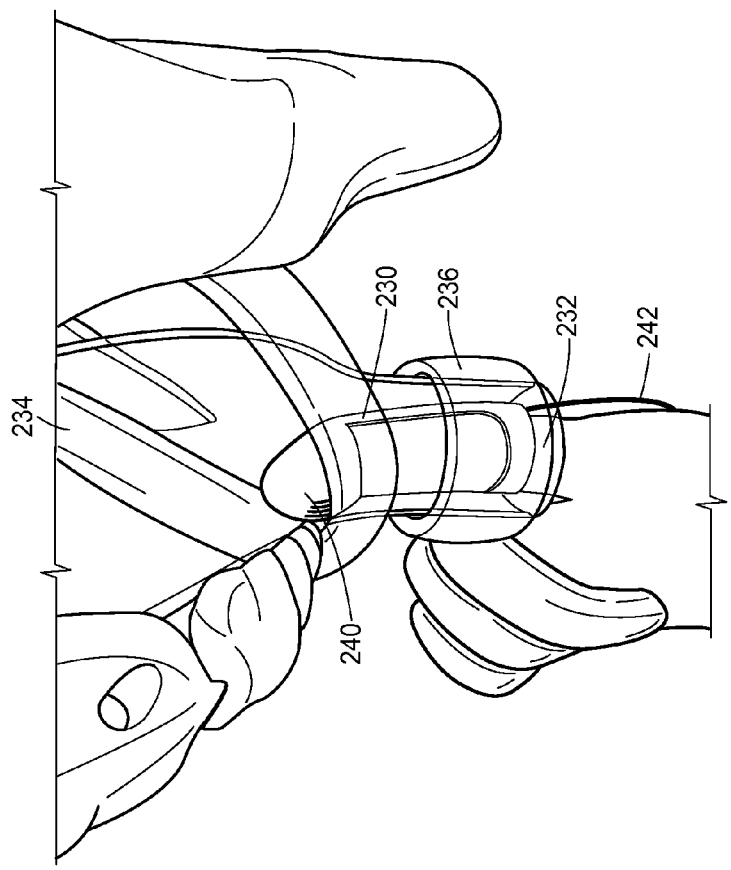
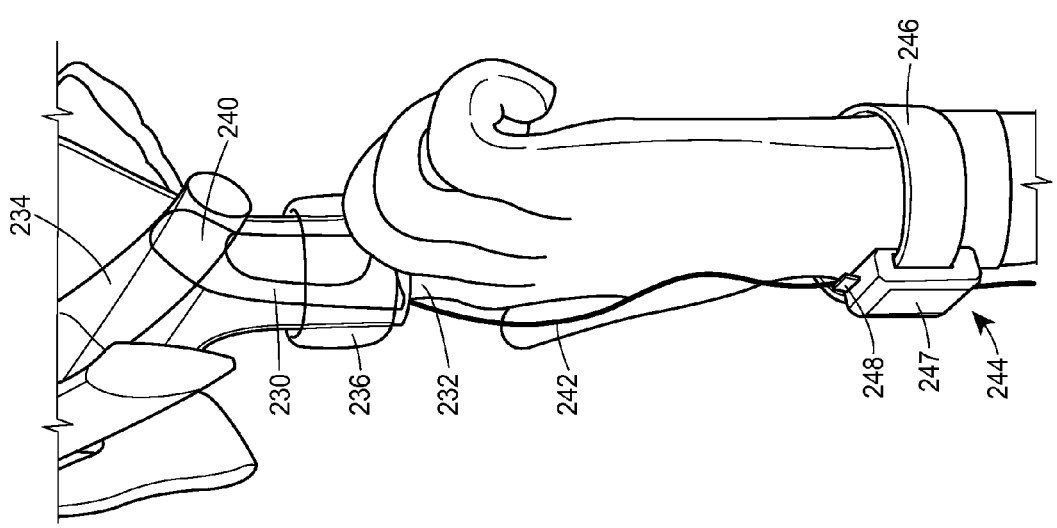

DIGITAL MANOMETRY FINGER-MOUNTABLE SENSOR DEVICE

CROSS-REFERENCE TO RELATED APPLICATION

The present application claims the benefit of U.S. Patent Application No. 61/576,779 filed Dec. 16, 2011, the disclosure of which is incorporated herein by reference in its entirety for all purposes.

GOVERNMENT LICENSE RIGHTS

This work was supported by the U.S. Department of Veterans Affairs, and the Federal Government has certain rights in this invention.

TECHNICAL FIELD

The present application relates generally to diagnosing medical conditions and, more specifically, to a method and system for diagnosing an anorectal disorder of a patient.

BACKGROUND

Anorectal disorders including constipation and fecal incontinence are common, embarrassing, and sometimes disabling gastrointestinal (GI) complaints. Constipation can involve a variety of symptoms such as excessive straining, hard stools, feeling of incomplete evacuation, use of digital maneuvers, and infrequent defecation. Fecal incontinence is defined as the unintentional loss of solid or liquid stool. Chronic constipation is one of the most common GI complaints of patients, being reported in 10 to 15% of the adult population in the United States. Fecal incontinence is also common, being reported in 6 to 10% of the adult population in the United States. The prevalence of both conditions appears to be greater in females and increases with age. In addition, both chronic constipation and fecal incontinence are often attended by decreased quality of life, decreased work productivity, and increased health care costs.

Chronic constipation may be divided into two main physiological subgroups: slow-transit constipation (colonic inertia) and dyssynergic defecation. Some patients (e.g., patients with irritable bowel syndrome) may exhibit features of both of these types of chronic constipation. Patients with slow-transit constipation may exhibit impaired phasic colonic motor activity, diminished gastrocolonic responses after a meal, abnormal colonic motor activity upon waking, and underlying neuropathy as demonstrated by a paucity of interstitial cells of Cajal (ICC). Patients with dyssynergic defecation may exhibit abnormal coordination of abdominal, rectoanal, and pelvic floor muscles when attempting to defecate, as well as impaired rectal sensation.

Available laxative therapies are primarily aimed at improving colon transit and secretion, and offer only limited efficacy to patients with dyssynergic defecation. For dyssynergic defecation, biofeedback training has been shown to be far superior to laxative therapy. Unfortunately, current tools for diagnosing dyssynergic defecation are not widely available, require dedicated infrastructure, are expensive, rely on limited data/measurements, and/or involve complicated data analysis. One tool that suffers from these deficiencies, despite being widely considered as the current "gold standard" for diagnosing dyssynergic defecation, is the anorectal manometry (ARM) system. ARM systems, which are catheter-based systems that monitor the anal sphincter to assess abnormal contractions, are often not accessible. Even when available, ARM systems are cost-prohibitive for many patients and health care providers.

Given the expense of accurately diagnosing dyssynergic defecation, primary care physicians and most GI specialists simply prescribe a laxative and suggest dietary restrictions to patients complaining of symptoms indicative of constipation (excessive straining, hard stools, etc.). Primary care physicians may only refer a patient to a GI specialist with proper diagnostic tools, and GI specialists may only utilize those tools, after such therapies have been proven ineffective. By that time, however, the patient may have incurred a significant amount of health care costs, and the patient's symptoms may have intensified. Further, the patient is then subject to the considerable expense associated with using current diagnostic tools (e.g., the ARM system) before receiving biofeedback or other therapies that are most appropriate for the specific condition of the patient. Thus, the lack of an accurate, lower-cost diagnostic tool for health service providers can lead to additional cost, time, and suffering for patients.

Fecal incontinence can arise as a consequence of nerve or muscle damage involving the pelvic floor and/or anal sphincter. A variety of other factors, including obesity, physical inactivity, genetic factors, comorbid diseases which affect neuromuscular function or cause diarrhea, and previous trauma, have been associated with fecal incontinence. Assessment of the pelvic floor and anal sphincter muscles is critical to the evaluation of patients with fecal incontinence. Discovery of reduced anal sphincter pressure at rest or when attempting to voluntarily squeeze the anal sphincter muscle can identify patients who might benefit from physical therapy and biofeedback aimed at strengthening the anal sphincter and pelvic floor muscles. While some of this information can be gleaned from a detailed digital rectal examination, as with dyssynergic defecation most primary care physicians and GI specialists are not properly trained to perform this type of evaluation. Even when a provider is trained to perform a detailed digital rectal examination, findings in patients with fecal incontinence are often subtle and difficult to definitively identify without the use of more quantitative testing with anorectal manometry. Unfortunately, all of the issues involving accessibility, infrastructure, and cost that are problematic for using anorectal manometry to identify dyssynergic defecation are also operative in the evaluation of patients with fecal incontinence.

BRIEF DESCRIPTION OF THE DRAWINGS

FIG. 4 is a set of schematics for the example finger-mountable sensor device of FIGS. 3A-3C.

FIGS. 7A and 7B are diagrams of an example finger-mountable sensor device in operation.

DETAILED DESCRIPTION

Figure 1:
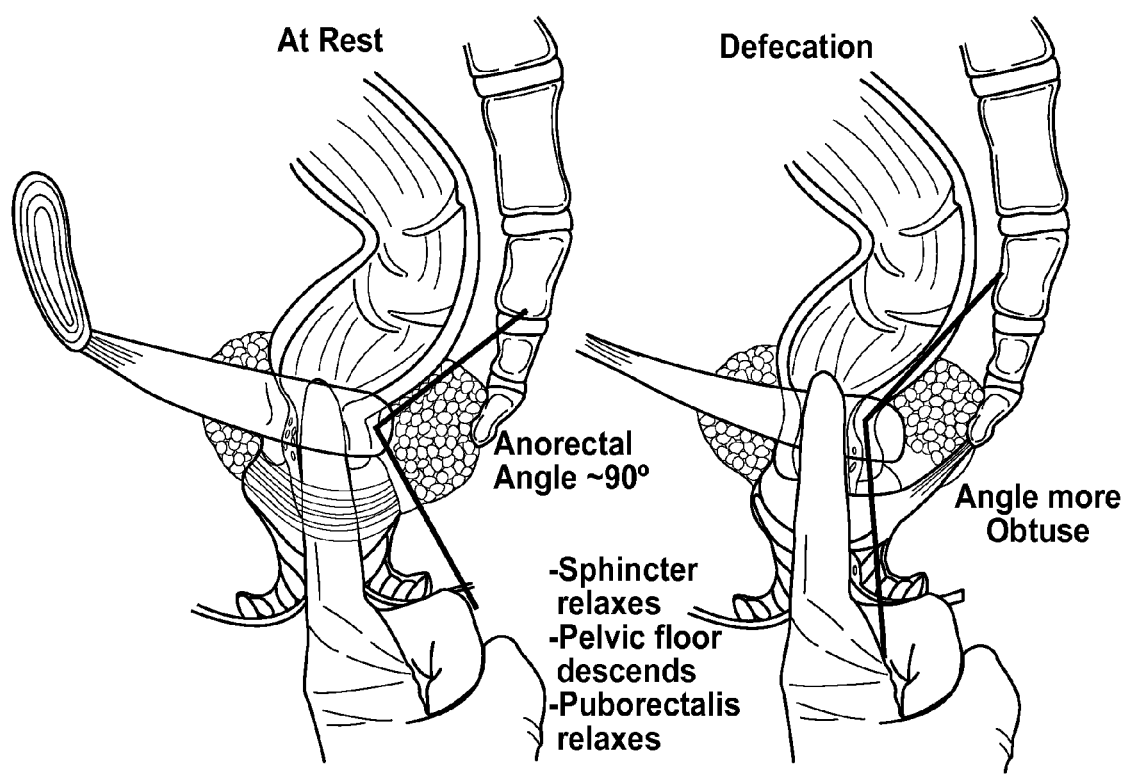
FIG. 1 illustrates normal anorectal physiology while at rest and during simulated defecation.

FIG. 1 illustrates normal anorectal physiology while at rest and during defecation or simulated defecation. "Simulated defecation" refers to a state in which the patient being observed makes an effort to defecate without actually defecating. As shown in FIG. 1, defecation (simulated or otherwise) by an individual having a normal, healthy anorectal physiology involves a number of physiological processes, including relaxation of the puborectalis muscle (leading to an increase in the anorectal angle from roughly 90 degrees to a more obtuse angle) and lowering of the pelvic floor or perineum, as well as relaxation of the anal sphincter muscle. Further, the diaphragm and abdominal wall musculature contract, increasing intrarectal pressure.

Figure 2:
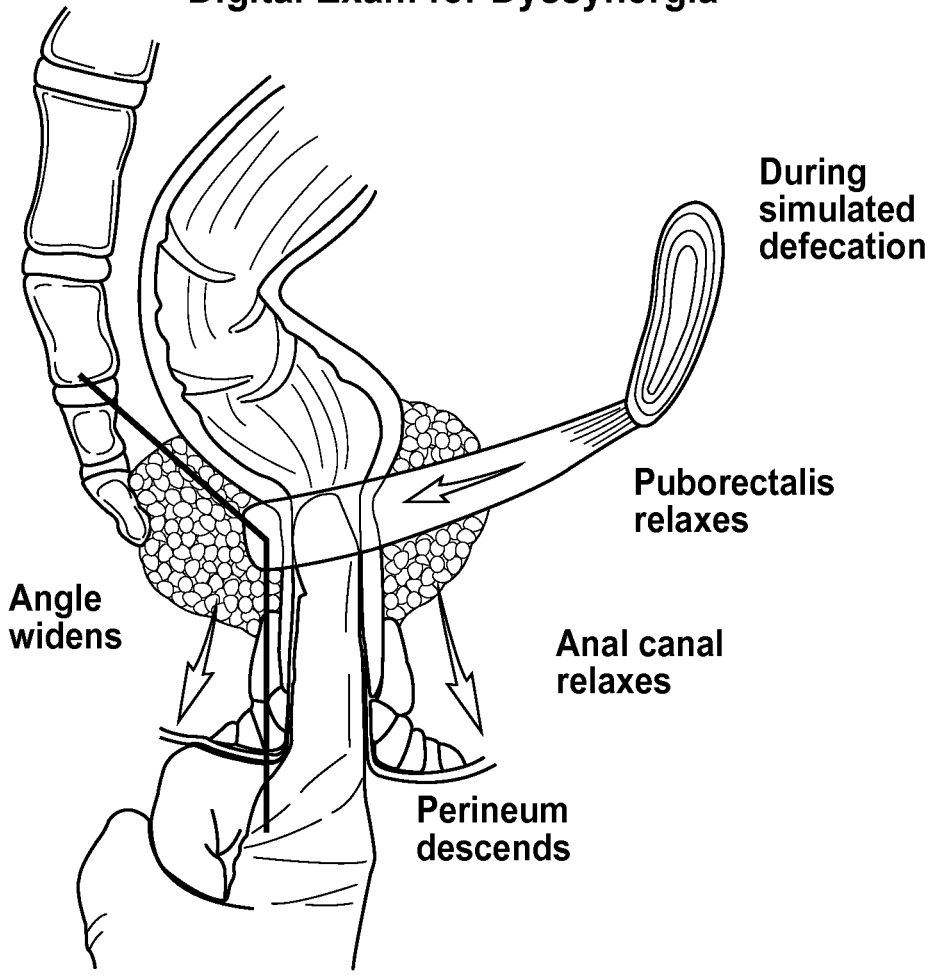
FIG. 2 illustrates a digital examination for determining whether a patient exhibits symptoms of dyssynergic defecation.

FIG. 2 illustrates a digital examination for determining whether a patient exhibits symptoms of dyssynergic defecation. Typically, a physician performs such an examination by inserting his or her finger into the rectum of the patient, as shown in FIG. 2. The physician's finger (and entire hand) is covered by a protective layer, such as a surgical glove, that preserves the physician's tactile sensitivity (i.e., ability to discriminate between shapes, textures, etc., using the sense of touch). While the physician's finger is inserted in the patient's rectum, the physician instructs the patient to attempt to defecate, or "push" as if the patient were defecating. FIG. 2 depicts a simulated defecation state in which a patient with normal anorectal physiology is making such an effort. Because the patient of FIG. 2 exhibits normal anorectal physiology, the puborectalis has relaxed, the anorectal angle has widened, the perineum has descended, and the anal sphincter muscle has relaxed, relative to the patient's overall relaxed (i.e., non-simulated defecation) state.

Unassisted, a physician has a very limited ability to detect the physiological processes associated with simulated defecation. For example, while the physician may be able to sense whether his or her finger is being pushed out of the rectum during simulated defecation (as occurs for patients having a normal anorectal physiology), the lack of a qualitative, standardized assessment would often lead to misinterpretation (i.e., over- or under-interpretation) and a highly subjective diagnosis. Moreover, each patient's physiology may be different, meaning that the level of pressure applied by one patient experiencing dyssynergic defecation may be notably different than another patient experiencing dyssynergic defecation, or may be the same as another patient experiencing normal defecation. Furthermore, primary care physicians and most GI specialists are not trained to perform a detailed digital rectal exam, as described above.

The disclosed system utilizes a device to be mounted on a finger of a user (e.g., a physician) and, in some embodiments, also utilizes one or more external processing components. The finger-mountable device includes one or more sensors, each configured to measure a physical characteristic (e.g., pressure or biopotential) of a tissue (e.g., muscle tissue) in a patient. Each sensor outputs one or more signals corresponding to the measured characteristic. The output signals from the sensor(s) may be processed (e.g., by a personal computer running a software application) to provide information that is useful in diagnosing whether the patient has a particular anorectal disorder, such as dyssynergic defecation, reduced sphincter function, stool soiling or fecal incontinence, etc.

Figure 3A:
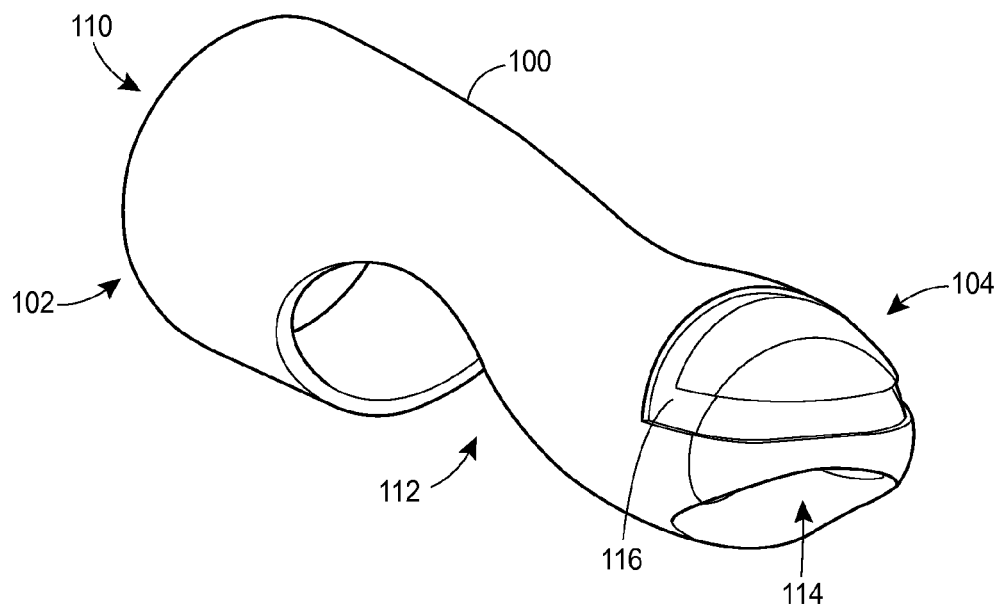
FIG. 3A is a diagram of an inner layer of a housing of an example finger-mountable sensor device.
Figure 3B:
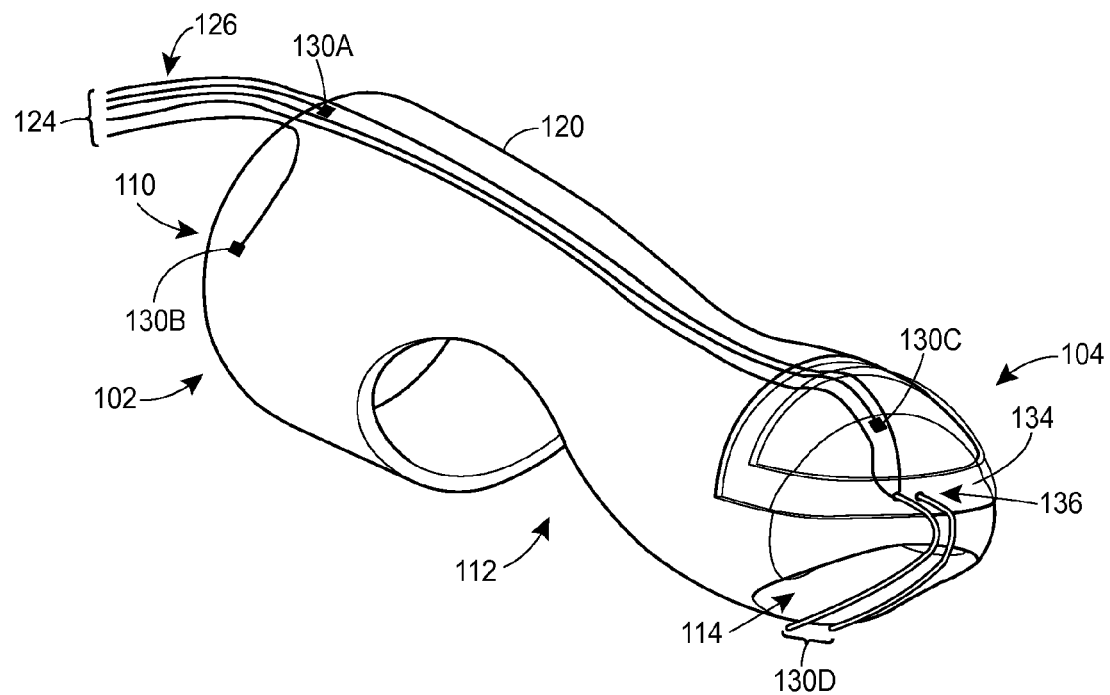
FIG. 3B is a diagram of a middle layer of a housing of an example finger-mountable sensor device.
Figure 3C:
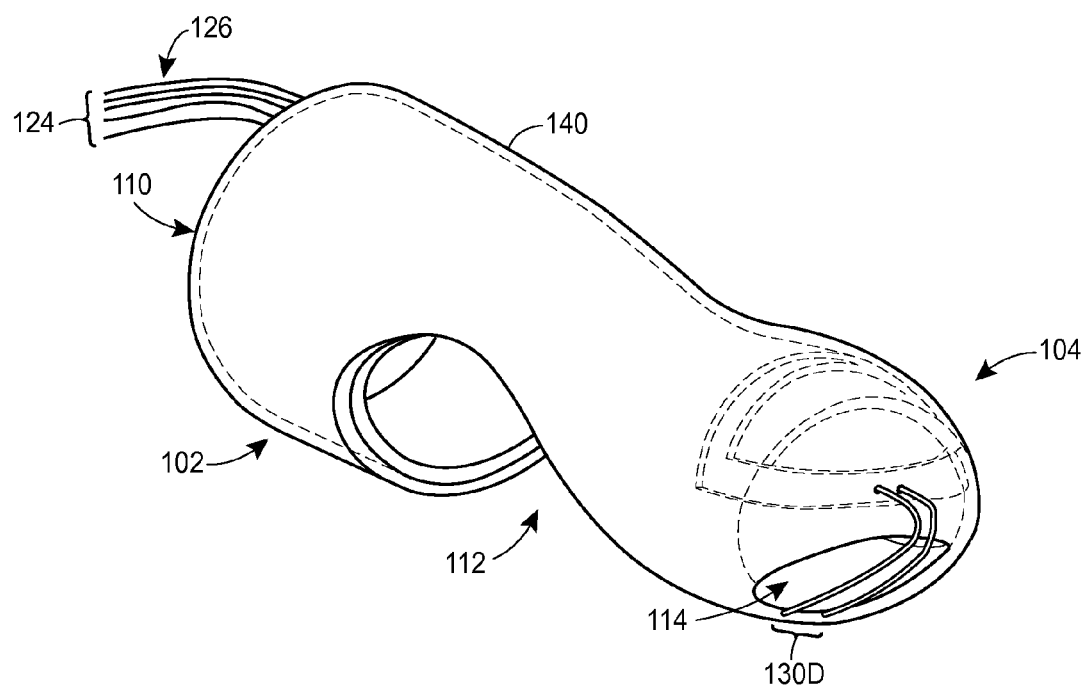
FIG. 3C is a diagram of an outer layer of a housing of an example finger-mountable sensor device.

FIGS. 3A-3C are diagrams of inner, middle, and outer layers, respectively, of a housing of an example finger-mountable sensor device. As shown in FIG. 3A, an inner layer 100 of the housing is generally finger-shaped, having a proximal receptacle end 102 and a distal end 104. The proximal receptacle end 102 defines a first opening 110 into which a physician can insert his or her finger (e.g., an index finger). The physician's finger may be covered with a protective layer (e.g., the physician may wear a polyisoprene surgical glove) prior to insertion into the housing of the finger-mountable device. In an embodiment, the opening 110 in the proximal receptacle end is present in each layer of the housing.

In an embodiment, the inner layer 100 is composed of a material sufficiently flexible to allow the physician to flex his or her finger a substantial amount when wearing the device. As an example, the inner layer 100 may be composed of silicone. As another example, the inner layer 100 may be composed of polyurethane. In some embodiments, the inner layer 100 is composed of more than one material.

The housing of the embodiment illustrated in FIG. 3A includes two openings in addition to the first opening 110 at the proximal receptacle end. A second opening 112 generally aligns with the palmar side of the proximal interphalangeal joint of a finger inserted into the device, and facilitates flexion of the physician's finger. In an embodiment, the second opening 112 (in combination with the flexibility of the materials used in each layer of the housing) allows a physician wearing the device to flex his or her finger at least 90 degrees. In an embodiment, the second opening 112 extends through all layers of the housing (e.g., inner, middle, and outer layers for a three-layer housing). In another embodiment, the second opening 112 extends through only a subset of layers (e.g., only the inner and/or middle layer) of the housing. In yet another embodiment, each layer of the entire housing is constructed of material(s) sufficiently flexible to allow a physician wearing the device to flex his or her finger at least 90 degrees even without the second opening 112.

A third opening 114 generally aligns with the pad of the physician's fingertip (i.e., opposite the physician's fingernail), and allows the physician to maintain tactile sensitivity when wearing the device. In an embodiment, the third opening 114 extends through all layers of the housing (e.g., inner, middle, and outer layers). In another embodiment, the third opening 114 extends through only a subset of layers (e.g., only the outer and/or middle layer) of the housing. In yet another embodiment, some layers of the housing include the third opening 114, but at least one layer (and/or a separate piece of material) provides a membrane that covers the third opening 114 with a material that allows the physician to maintain tactile sensitivity (e.g., polyisoprene). In an embodiment, the third opening 114 is approximately 6.5 mm in a direction from fingertip towards the finger base, and approximately 15.7 mm in an orthogonal direction across the fingertip pad.

While the inner layer 100 illustrated in FIG. 3A includes three openings 110, 112 and 114, other embodiments include more or fewer openings. For example, the inner layer 100 may include only the opening 110 at the proximal receptacle end. As another example, the inner layer may include a fourth opening in the housing (e.g., a dorsal-side opening opposite the second opening 112 described above, to provide even greater flexibility of the physician's proximal interphalangeal joint). In some embodiments, the edges of some or all of the openings are graded.

In an embodiment, the finger-mountable device includes a support (not shown in FIG. 3A) at the distal end 104 of the device that is relatively rigid as compared to the rest of the housing layers. For example, as shown in FIG. 3A, a groove 116 for the support may be located opposite the third opening 114 described above (i.e., the support may be generally aligned with the fingernail of the inserted finger). The support itself is discussed in more detail below.

A middle layer 120 of the housing of the finger-mountable device, as shown in FIG. 3B, is disposed radially outward of the inner layer 100 shown in FIG. 3A. In an embodiment, the middle layer 120 is immediately adjacent to and in contact with the inner layer 100 substantially along the entire inner surface of the middle layer 120. In an embodiment, the inner surface of the middle layer 120 is attached to the outer surface of the inner layer 100 by an adhesive. As explained above, the middle layer 120 may include openings that generally align with some or all of the openings (e.g., openings 110, 112 and/or 114) in the inner layer 100.

In an embodiment, the middle layer 120 is composed of a material sufficiently flexible to allow the physician to flex his or her finger a substantial amount (e.g., greater than 90 degrees) when wearing the device, either with or without the opening 112 at the interphalangeal joint according to the embodiment. As an example, the middle layer 120 may be composed of high-density polyethylene (HDPE). As another example, the middle layer 120 may be composed of polypropylene (PP). In some embodiments, the middle layer 120 is composed of more than one material.

The housing of the finger-mountable device carries a probe assembly 124 having wires 126 coupled to one or more sensors 130. In some embodiments, some or all sensors 130 and/or wires 126 of the probe assembly 124 are mounted on, or embedded within, a layer of the housing. In some embodiments, some or all of the sensors 130 and/or wires 126 of the probe assembly are instead merely mounted on the external surface of a single housing layer, such as the layer 100. In some embodiments, some or all of the sensors 130 and/or wires 126 of the probe assembly are instead merely sandwiched between two housing layers. In the example embodiment of FIGS. 3A-3C, the middle layer 120 of the housing carries the probe assembly 124, as shown in FIG. 3B. A pair of sensors 130A and 130B measures anal sphincter muscle tissue pressure, another sensor 130C measures intrarectal pressure, and a puborectalis activity sensor 130D comprising a pair of EMG electrodes measures a differential voltage.

In some embodiments, the probe assembly 124 includes a probe layer (not shown in FIG. 3B) separate from the other layers of the housing. The probe layer may include a substrate on which the sensors 130 of the probe assembly 124 are supported or mounted, for example. In some embodiments, sensors (e.g., pressure sensors such as sensors 130A-130C) are wire-bonded to pads on the substrate. In some embodiments, electrodes of sensors (e.g., EMG sensors such as sensor 130D) are formed as conductive traces on the substrate (or are metal strips or wires that extend from the substrate, etc.). In some embodiments, the substrate of the probe layer forms a printed circuit board or flex circuit, which in turn includes electrical leads for connecting the probe assembly to a controller assembly (discussed below) through an electrical receptacle.

The anal sphincter pressure sensors 130A-130B of FIG. 3B are disposed at different locations along a circumference of the middle layer 120 of the housing, at the proximal end 102 of the housing. In other embodiments, the finger-mountable device includes only a single anal sphincter pressure sensor or more than two anal sphincter pressure sensors, and/or the sensor(s) are carried by a different layer of the housing.

The intrarectal pressure sensor 130C of FIG. 3B is disposed at the distal end 104 of the housing (e.g., adjacent a fingernail position of the fingertip to measure pressure on a nail side of the physician's finger). In other embodiments, the finger-mountable device includes multiple intrarectal pressure sensors, and/or the sensor(s) are carried by a different layer of the housing. One or both of the anal sphincter pressure sensor(s) 103A-130B and the intrarectal pressure sensor 130C comprise one or more pressure sensor die, in an embodiment. In an embodiment, some or all of the pressure sensors 130A-130C can detect pressure variations over at least a −50 to +300 mmHg range.

The puborectalis activity sensor 130D of FIG. 3B comprises a pair of EMG electrodes in a differential configuration that are disposed at the distal end 104 of the housing. In an embodiment, the EMG electrodes of the puborectalis activity sensor 130D span all or a part of the third opening 114 in the housing (described above in connection with FIG. 3A). For example, the electrodes may create a path that divides the third opening 114 approximately into two halves of equal area. In some embodiments, the finger-mountable device includes multiple puborectalis activity sensors (e.g., multiple pairs of EMG electrodes), and/or the puborectalis activity sensor(s) are carried by a different layer of the housing. In an embodiment, some or all of the activity sensors can detect voltage variations over at least a 0 to 250 μV range.

In an embodiment, the EMG electrodes of the puborectalis activity sensor 130D are wires made of a conductive, biocompatible material (e.g., silver). In another embodiment, the EMG electrodes of the puborectalis activity sensor 130D are flat strips of a conductive, biocompatible material (e.g., silver). In various embodiments, the diameter (for a wire) or width (for a strip) of each electrode is 0.3, 0.55, 0.8, 1.04, 1.44, or 1.85 mm. Electrode strips are 0.23 mm thick, in one embodiment. In various embodiments, the electrode wires or strips of an electrode pair are spaced 2, 4, 6, or 8 mm apart. In one embodiment, the electrode diameter or width is 0.3 mm and the electrode spacing is 4 mm. In another embodiment, the electrode diameter or width is 1.44 mm and the electrode spacing is 4 mm. In another embodiment, the electrode diameter or width is 1.85 mm and the electrode spacing is 6 mm.

While the example middle housing layer 120 of FIG. 3B depicts a single, bipolar pair of EMG electrodes in the puborectalis activity sensor 130C, other embodiments may include an EMG sensor having a double differential configuration. The double differential configuration includes two pairs of EMG electrodes in parallel, designated herein as first electrode pair A, B and second electrode pair C, D for ease of explanation. In some embodiments that include a double differential configuration, a first differential amplifier with a high common-mode rejection ratio amplifies the difference between the electrodes A and B, a second, matched differential amplifier with a high common-mode rejection ratio amplifies the difference between the electrodes C and D, and a third differential amplifier amplifies the difference between the outputs of the first and second differential amplifiers. In this manner, background noise that is common to the electrodes A, B, C and D is rejected, resulting in a cleaner EMG signal. As discussed further below, the differential amplifiers may be at a location external to the probe device, in some embodiments.

In use, the physician inserts a finger into the finger-mountable sensor device prior to insertion, and then inserts both finger and device into the rectum of the patient. When the finger and device are fully inserted (or, at least, are inserted to a sufficient degree such that one or more sensors 130 on the device are properly located within the patient), each of the sensors 130 of the probe assembly 124 provides data on pressure or function (e.g., potential) of the sphincter or rectum. The anal sphincter pressure sensors 130A-130B are located proximate the anal sphincter muscle to measure pressure applied by the anal sphincter muscle. The intrarectal pressure sensor 130C is located on the fingertip adjacent to the nail bed to measure pressure within the rectal lumen caused by intra-abdominal pressure resulting from diaphragm and/or abdominal muscle contractions. The electrodes of the puborectalis activity sensor 130D are located proximate the puborectalis muscle, and measure a voltage differential across tissue contacted by the electrodes. In some embodiments, the various sensors 130 measure the pressure or voltage at a first time when the patient is in a relaxed state, and at a second time when the patient is in a simulated defecation state. In some embodiments, the various sensors 130 also measure the pressure or voltage at a third time when the patient is asked to maximally contract the puborectalis muscle so as to close the anal canal as tightly as possible.

The middle layer 120 of the housing includes a support 134 as referenced above in connection with FIG. 3A. In other embodiments, the support 134 is instead included in the inner layer 100 or a different layer of the housing, or is included in multiple housing layers. In various embodiments, the support 134 may be included in a housing layer by embedding the support 134 within the material of the layer, or by using adhesive to attach the support 134 to the layer. In the embodiment of FIGS. 3A-3C, the support 134 rests in the groove 116 of the housing inner layer 100, and extends through the housing middle layer 120.

The support 134 may comprise a frame defining an interior opening, as shown in FIG. 3B, or comprise a flat piece without an interior opening, in various embodiments. In an embodiment, the support 13 is relatively rigid as compared to the rest of the housing layers. For example, the support 134 may be formed of a metal or a hard plastic. In an embodiment, the support 134 is formed of HDPE. In some embodiments, the support 134 acts as a stabilizing member for the EMG electrodes of the puborectalis activity sensor 130D. For example, the support 134 may include one or more holes 136 through which each electrode passes, as illustrated in FIG. 3B. In this manner, the support 134 may maintain the spacing between the EMG electrodes.

As noted above, the probe assembly 124 includes wires 126 connected to the various sensors 130 in order to couple output signals from the sensors 130 to a controller assembly (discussed below). For example, in the embodiment of FIG. 3B, one or more of the wires 126 couples to each pressure sensor and one of the wires 126 couples to each EMG electrode. In an embodiment, some or all of the wires 126 are thin wires covered by insulating material. In some embodiments, some or all of the wires 126 are included in a different housing layer. In various embodiments, the wires 126 may be embedded within a housing layer, attached to the housing layer with adhesive, merely sandwiched between two housing layers, etc. In some embodiments, some of the wires 126 are soldered to substrates carrying the pressure sensors. The substrates may in turn be wire-bonded to pressure sensors that consist of die mounted on the substrates, for example.

In the illustrated example, an outer layer 140 of the housing of the finger-mountable device, as shown in FIG. 3C, is disposed radially outward of the middle layer 120 shown in FIG. 3B. In an embodiment, the outer layer 140 is immediately adjacent to and in contact with the middle layer 120 substantially along the entire inner surface of the outer layer. In an embodiment, the inner surface of the outer layer 140 is attached to the outer surface of the middle layer 120 by an adhesive, such as a silicone adhesive (e.g., NuSil® MED3-4013 silicone adhesive). As explained above, the outer layer 140 may include openings that generally align with some or all of the openings in the inner and/or middle layer (e.g., openings 110, 112 and/or 114).

In an embodiment, the outer layer 140 is composed of a material sufficiently flexible to allow the physician to flex his or her finger a substantial amount (e.g., greater than 90 degrees) when wearing the device, either with or without the opening 112 at the interphalangeal joint according to the embodiment. As an example, the outer layer 140 may be composed of silicone. In some embodiments, the outer layer 140 is composed of more than one material.

The outer layer 140 provides a smooth exterior and/or a gently contoured shape to facilitate insertion of the device (when worn on a physician's finger) into the rectum of a patient. In an embodiment, the contoured shape is shared by all of the housing layers.

While FIGS. 3A-3C depict a housing with a probe assembly 124 that includes anal sphincter pressure sensors 130A-130B, an intrarectal pressure sensor 130C, and a puborectalis activity sensor 130D, other embodiments may include fewer types of sensors. For example, the probe assembly may include only the intrarectal pressure sensor 130C and/or the puborectalis activity sensor 130D, in some embodiments. Moreover, some embodiments may include additional types of sensors, and/or may include the same types of sensors but at different locations. For example, the probe assembly 124 may instead (or additionally) include an EMG sensor at the proximal end 102 of the finger-mountable device (e.g., for internal or external EMG measurements of the anal sphincter). As other examples, the probe assembly 124 may instead (or additionally) include one or more inertial sensors that measure velocity and/or acceleration of one or more body tissues, and/or may include one or more adjustable-length pressure sensors.

In some embodiments, the probe assembly 124 includes a pH sensor/detector, which a physician (or an automated algorithm) may use to determine whether bacteria in a patient's colon is interacting with digested foods in a normal manner. For example, bacteria in the colon normally ferments carbohydrates to produce short-chain fatty acids, which should lead to a more acidic pH level.

In some embodiments, the probe assembly 124 includes an osmolality sensor. Osmolality is a measure of the osmoles of solute per kilogram of solvent, and is typically expressed in units of osmol/kg or Osm/kg. The osmolality sensor may measure the osmoles of various kinds of particles in blood or in other bodily fluids, for example.

In some embodiments, the probe assembly 124 includes one or more sensors for detecting the stiffness or elasticity (e.g., elastic modulus) of a patient's rectum. For example, the probe assembly 124 may measure stiffness or elasticity by including one or more sensors for ultrasound elastography (e.g., the probe assembly may include one or more ultrasound transducers, with or without a force or pressure transducer to measure the palpation force). As another example, the probe assembly 124 may measure the relationship between the force required to indent the tissue of interest and the extent to which that tissue of interest has conformed to the indenting part, as measured by multiple sensors mounted around the circumference of the finger-mountable device. An algorithm may use the data from these sensors, along with data from one or more pressure sensors (e.g., at or near the position of the physician's fingertip pad within the finger-mountable device) to calculate elasticity of tissue being palpated by the physician, for example. Whether stiffness/elasticity is measured by ultrasound elastography or other types of sensors, the data may be used by the physician (or an automated algorithm) in combination with anal sphincter pressure data (e.g., from anal sphincter pressure sensors on the finger-mountable device) to diagnose fecal incontinence, for example.

The various sensors types described above, including inertial, pH, osmolality and/or stiffness/elasticity sensors, may be placed at any location(s), relative to the housing, that is/are appropriate given the parameter or characteristic that the sensor is intended to measure. For example, a pH or osmolality sensor may be located more distally (i.e., closer to the distal end 104) in order to obtain better measurements.

In still other embodiments, the probe assembly 124 includes an array of pressure sensors extending from the distal end 104 to the proximal end 102 of the finger-mountable device for high-resolution manometry. For example, the probe assembly 124 may include an array of pressure sensors extending in a generally spiral fashion (or as a series of generally concentric rings) around the housing of the finger-mountable device from the distal end 104 to the proximal end 102 (or some portion thereof). By closely spacing the sensors of the array, the array may provide data for creating a high-resolution topographic pressure map. In some embodiments, the array includes at least 40 sensors (e.g., between 40 and 50 sensors). In some embodiments, each sensor is spaced one centimeter or less from the next nearest sensor in the array.

In some embodiments, the probe assembly 124 includes an angle sensor. The puborectalis muscle generally passes in a "U" shape from the right front side of the pelvis, around the back of the rectum, to the left front side of the pelvis, and crimps or restricts the anal canal to cause a change in angle between the posterior margin of the distal rectum and the anal sphincter when the puborectalis muscle contracts or relaxes, as shown in FIGS. 1 and 2. In an embodiment, the angle sensor of the probe assembly 124 determines this change in angle.

While FIGS. 3A-3C depict a housing that consists of three layers, more or fewer layers may be used in other embodiments. For example, the housing may include only a single layer, four layers, etc., in some embodiments. In an embodiment, the maximum total thickness of the housing of the finger-mountable device (including all housing layers, and including any thickness added by the probe assembly) is less than 3 mm. In an embodiment, the materials of the housing (e.g., housing layer materials, wires, and/or sensors) are compliant with a biocompatibility standard (e.g., AAMI 10933). Moreover, in various embodiments, the thickness, material(s), and/or precise shape(s) of one or more layers of the housing may be designed so as to provide a desired rigidity, conformance to a physician's finger, tactile "feel" through the housing, and/or other desired characteristics, while maintaining a suitable level of sensitivity for various pressure sensors of the housing.

FIG. 4 is a set of schematics for one embodiment of the example finger-mountable sensor device shown in FIGS. 3A-3C. The schematics depict example viewpoints and dimensions of a silicone inner layer, an HDPE support, and a silicone outer layer.

Figure 5:
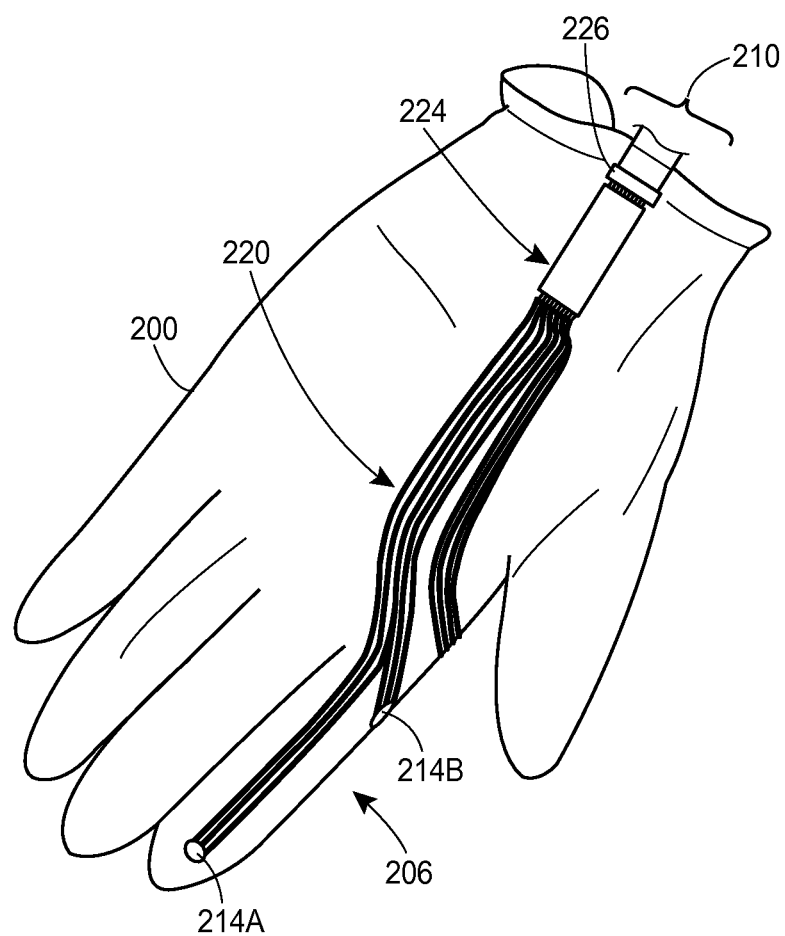
FIG. 5 is a diagram of another example finger-mountable sensor device.

FIG. 5 is a diagram of another example finger-mountable sensor device. Unlike the example device with the housing layers of FIGS. 3A-3C, which is configured to mount onto only a single finger of a physician, the example device includes a glove 200 configured to accept an entire hand of the physician. The glove 200 is made of a suitably flexible or elastic material, such as polyisoprene or nitryl, for example. In the example embodiment of FIG. 5, an index finger 206 of the glove 200 serves as a housing for an index finger of the physician, while also carrying a probe assembly 210 that includes sensors 214, traces 220 and a connector 224 with a plug receptacle 226. In other embodiments, a different finger of the glove 200, other than the index finger 206, serves as the housing that carries the sensors 214 of the probe assembly 210. In an embodiment, the index finger 206 includes an opening at the fingertip pad similar to the third opening 114 of FIG. 3A, in which case the physician's hand is preferably protected by an additional glove before putting on the glove 200.

The sensors 214A and 214B may be similar to the sensors 130C and 130B of the device of FIGS. 3A-3C, for example. In an embodiment, the sensors 214A and 214B are both pressure sensors, which may be sensor chips each mounted to a separate, small (e.g., 3 mm length and/or width, 1 mm thickness) circuit board. The circuit boards may in turn be fixed to the external surface of the glove 200 using a biocompatible adhesive, with conductive epoxy connecting the sensor chips and circuit boards to the appropriate traces 220. The sensor chips, circuit boards, and conductive epoxy (that couples the sensor chip to the traces 220) may be covered with a biocompatible waterproofing layer of silicone (e.g., a roughly 6 mm diameter layer), for example.

Figure 6:
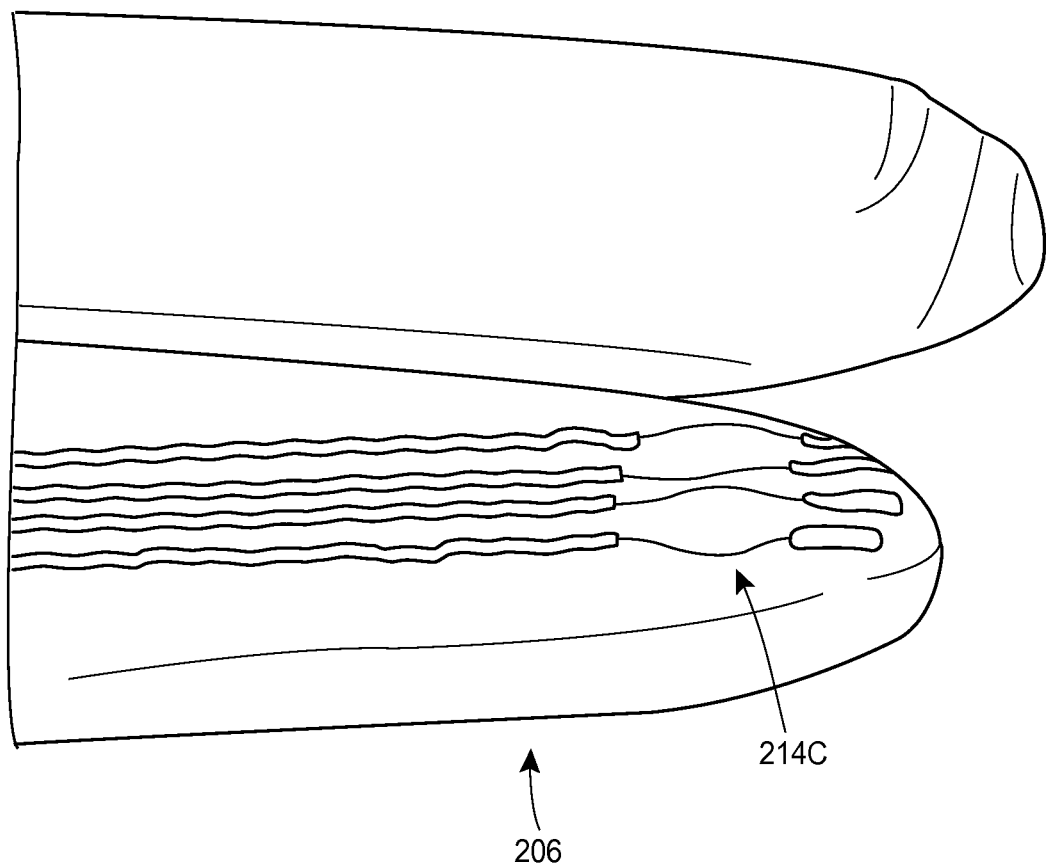
FIG. 6 is a diagram of a configuration of electrodes on the ventral surface of the example finger-mountable sensor device of FIG. 5.

A third, puborectalis activity sensor 214C of the probe assembly 210, located on the ventral surface of the example device of FIG. 5, is shown in FIG. 6. The puborectalis activity sensor 214C may be similar to the sensor 130D of the device of FIGS. 3A-3C, for example. While a double differential electrode configuration is shown in FIG. 6, other embodiments may include only a single electrode pair. In an embodiment, the electrode wires are fixed to the external surface of the glove 200 using a biocompatible adhesive.

Referring again to FIG. 5, the various sensors 214 are coupled to the traces 220, which couple to the connector 224. The traces may be formed from a flexible, conductive epoxy on the outer surface of the glove, for example. The plug receptacle 226 of the connector 224 may couple to a controller assembly (e.g., an assembly including filters and/or amplifiers strapped to the physician's wrist), as discussed in further detail below.

As discussed above in connection with the device of FIGS. 3A-3C, other embodiments may instead include a different number of sensors, different types of sensors, and/or sensors in different locations than the embodiment shown in FIGS. 5 and 6.

FIGS. 7A and 7B are diagrams of an example finger-mountable sensor device 230, such as the device of FIGS. 3A-3C, in operation. While FIGS. 7A and 7B show a finger-mountable device 230 that is similar to the device of FIGS. 3A-3C, it is understood that a different finger-mountable device may be used, such as the glove 200 of FIGS. 5 and 6.

After the physician inserts his or her gloved finger 232 into the finger-mountable sensor device 230 (or bare finger, for some embodiments in which the finger-mountable device itself is a glove or a part of a glove), the physician inserts both finger 232 and device 230 into the patient's rectum, such that any sensor(s) at the distal end of the device 230 (e.g., intrarectal pressure sensor and EMG electrodes) are in close proximity to the puborectalis muscle 234, and such that any sensors at the proximal end of the device (e.g., anal sphincter pressure sensor) are in close proximity to the anal sphincter muscle 236. To this end, the physician may palpate the (tensed) puborectalis 234 with a fingertip 240 to ensure his or her fingertip 240 is placed in the optimal (or a near-optimal) location. A tensed puborectalis 234 would be felt as a bulging sensation or an increased pressure on the fingertip 240.

The finger-mounted sensor device 230 is coupled to a controller assembly. The controller assembly may include analog and digital processing components, in some embodiments. For example, as shown in FIG. 7A, one or more wires 242 connected to the sensors of the finger-mountable sensor device 230 may be routed from the sensors to a wrist box 244 of the controller assembly, where the wrist box 244 is secured to the physician's wrist. The wrist box 244 may be secured to the physician via a Velcro® wrist strap 246, for example. In other embodiments, the box 244 may be secured to the physician via a belt clip or pocket clip. In some embodiments, the finger-mountable sensor device 230 includes a wireless transmitter that transmits sensor output signals to the wrist box 244, which includes a wireless receiver. In these embodiments, the finger-mountable sensor device 230 may be powered by one or more batteries (e.g., mounted to, or disposed within, the housing of the device 230), for example. In an embodiment, the wireless transmitter is embedded or otherwise included in the probe assembly of the finger-mountable sensor device 230 (e.g., embedded or otherwise included in a printed circuit board of a probe layer). In some embodiments, the probe assembly (e.g., a printed circuit board of a probe layer) includes a low voltage transformer configured to operate on output signals of one or more sensors in the probe assembly.

In an embodiment, the wrist box 244 includes a housing 247 having an attachment mechanism 248 (e.g., a plug receptacle) mounted to the housing 247 for removably attaching the wires or traces of the sensors (e.g., pressure sensors and EMG electrodes) to the wrist box 244. In some embodiments, the wrist box 244 includes circuitry that performs analog processing of one or more of the sensor output signals, such as amplification and/or filtering, as discussed in more detail below in connection with FIG. 9. In an embodiment, the wrist box 244 includes an output plug (not shown in FIGS. 7A and 7B) for removably coupling the wrist box 244 to a remaining portion of the controller assembly (also not shown in FIGS. 7A and 7B). For example, the wrist box 244 may include an output plug for connecting to a digital acquisition (DAQ) unit associated with a computer device, or may include (or be coupled to) a wireless transmitter for wireless coupling to the DAQ unit. The computer device (e.g., a personal computer) of the controller assembly is discussed in more detail below in connection with FIGS. 9 and 15.

Figure 8A:
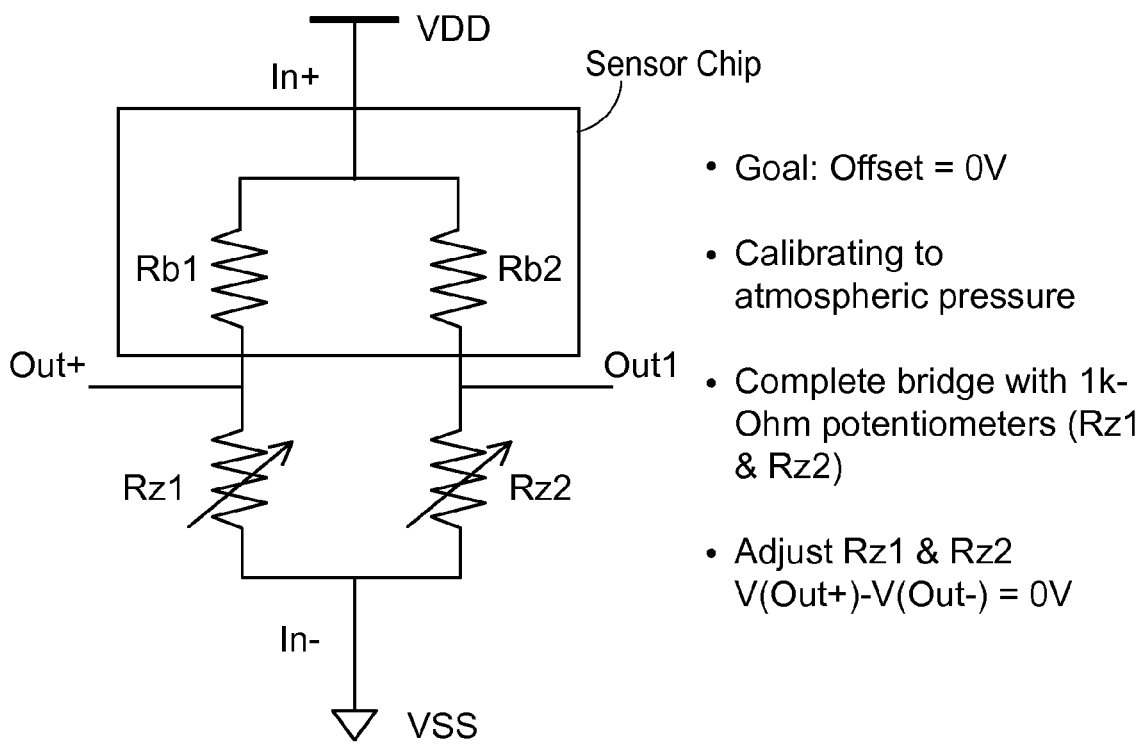
FIGS. 8A and 8B are diagrams of example circuits of a sensor calibration unit for one or more sensors of a finger-mountable sensor device.
Figure 8B:
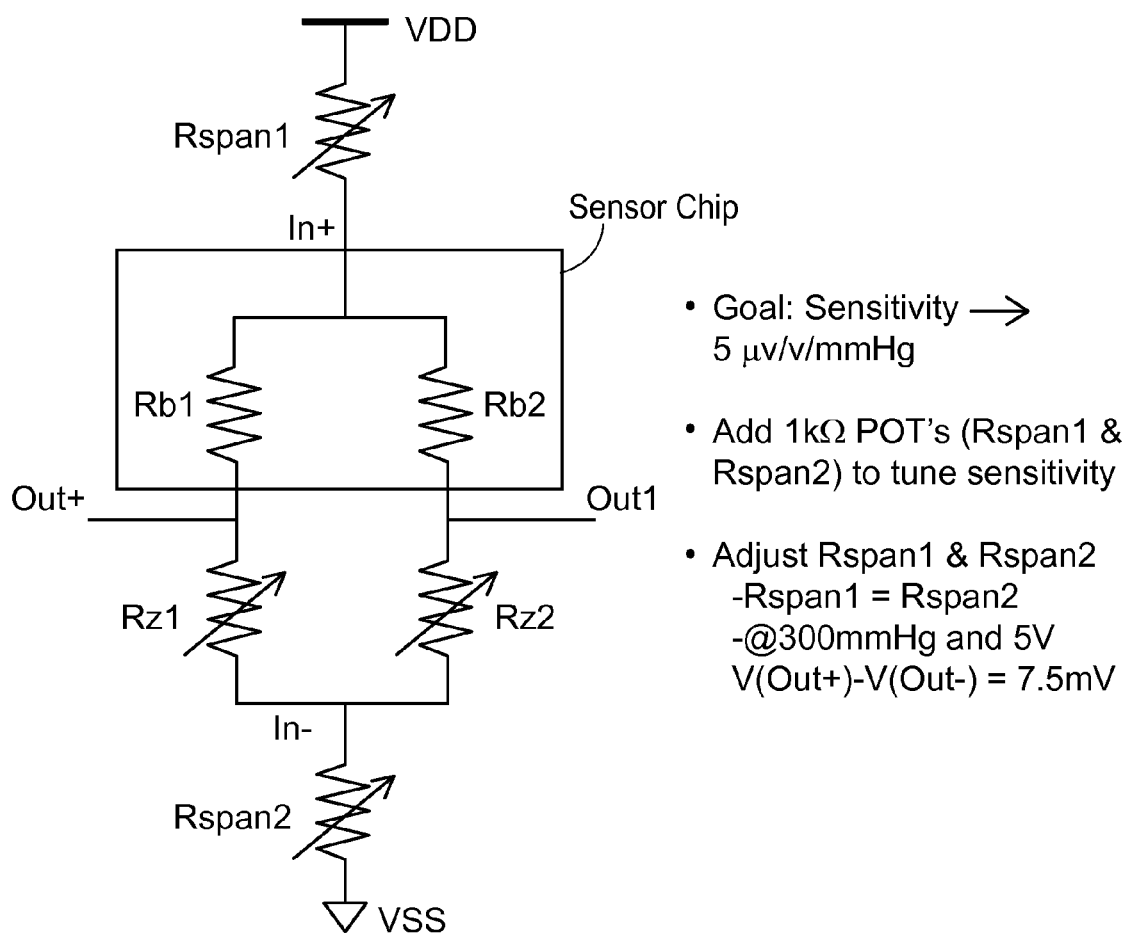

In some embodiments, a sensor calibration unit that is external or internal to the wrist box 244 can be adjusted for offset correction (e.g., to provide a 0 V differential output at atmospheric pressure) and/or sensitivity adjustment (e.g., to provide 5 µV/V/mmHg sensitivity) for output signals of pressure sensors included in the finger-mountable device 230. In an embodiment, the sensor calibration unit includes a separate calibration circuit for each pressure sensor. According to various embodiments, each calibration circuit can be manually or automatically adjusted. Example circuits of a sensor calibration unit are illustrated in FIGS. 8A and 8B, according to various embodiments. In an embodiment, the calibration unit circuitry is included on one or more integrated circuits.

Figure 9:
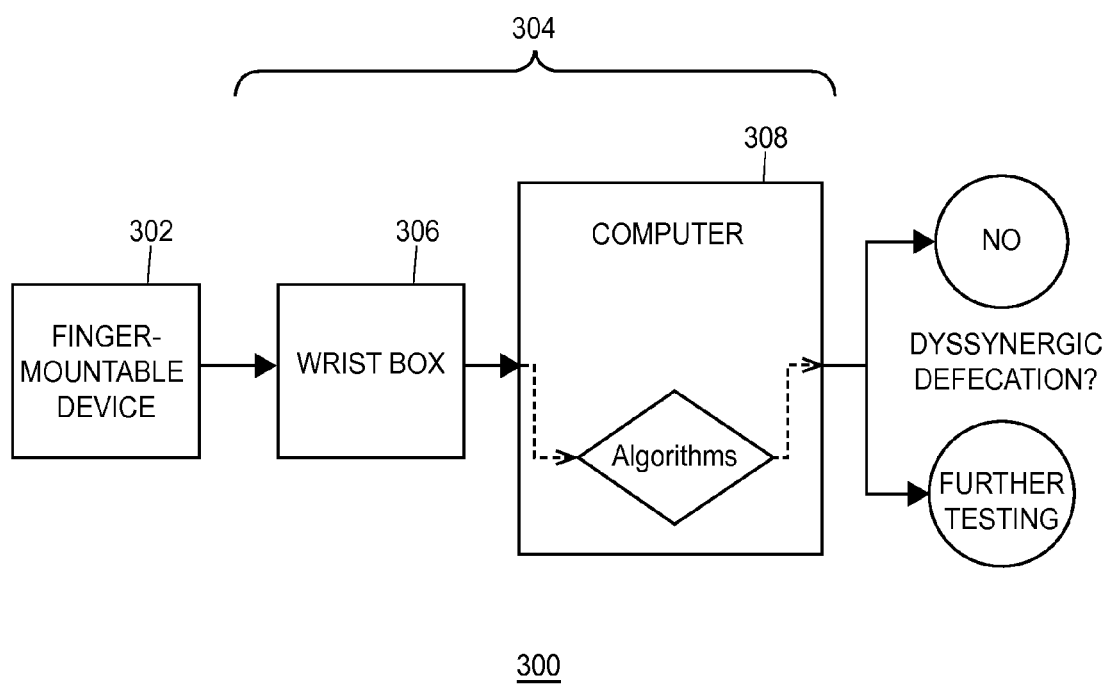
FIG. 9 is a block diagram of an example system for diagnosing an anorectal disorder.

FIG. 9 is a block diagram of an example system 300 for diagnosing an anorectal disorder, such as dyssynergic defecation. The system 300 includes a finger-mountable device 302 with sensors, such as the finger-mountable sensor device of FIGS. 3A-3C or FIGS. 5 and 6. The finger-mountable device 302 includes one or more anal sphincter pressure sensors, one or more intrarectal pressure sensors, and one or more puborectalis activity sensors, in some embodiments. In other embodiments, the finger-mountable device 302 only includes one of these sensors (e.g., an intrarectal pressure sensor) or two of these sensors (e.g., an intrarectal and anal sphincter pressure sensors).

The finger-mountable device 302 is coupled to a controller 304 assembly via a wired or wireless link. For example, as shown in FIG. 9, the controller 304 may include a wrist box 306. The wrist box 306 may be secured to the physician in a manner similar to the wrist box 244 illustrated in FIG. 7A, for example. In some embodiments, the wrist box 306 includes circuitry for analog processing (e.g., amplifying and/or filtering) of signals that are output by one or more sensors of the finger-mountable device 302. For example, the wrist box 306 includes one or more amplifiers coupled to one or more anal sphincter pressure sensors, one or more amplifiers coupled to one or more intrarectal pressure sensors, and one or more preamplifiers coupled to one or more puborectalis activity sensors (e.g., one or more pairs of EMG electrodes proximate the puborectalis), in some embodiments. The various preamplifiers and/or amplifiers may be connected to the appropriate sensors via wires or traces, such as the wires shown in FIG. 3B or the traces shown in FIGS. 5 and 6, for example. As another example, the wrist box 306 includes one or more bandpass or lowpass filters (e.g., one or more bandpass filters coupled to the puborectalis activity sensor(s), or coupled to one or more preamplifiers that are coupled to the puborectalis activity sensor(s)). In some embodiments, the wrist box 306 also includes or is coupled to a sensor calibration unit such as the sensor calibration unit of FIG. 8A or 8B.

In some embodiments, the controller assembly 304 also includes an additional amplifier or amplifiers (not shown in FIG. 9) coupled to the wrist box 306 to receive EMG electrode signals (e.g., EMG electrode signals that have been amplified by a preamplifier in the wrist box 306). In embodiments where the finger-mountable device 302 includes an EMG sensor having the double differential configuration discussed above, for example, the wrist box 306 may be coupled to the three differential amplifiers used to provide a clean EMG signal. In other embodiments, the amplifier(s) is/are included in the wrist box 306. In an embodiment, one or more electrical components of the system 200 (e.g., sensors, amplifiers, etc.) are compliant with an electrical safety standard (e.g., AAMI 60601-1).

In the example embodiment of FIG. 9, the controller assembly 304 further includes a computer device 308 including a housing and a processor, such as a personal computer (e.g., a laptop or desktop personal computer, or a personal digital assistant computer). In some embodiments, the computer device 308 is remote from the wrist box 306 and/or finger-mountable device 302, and is coupled to the wrist box 306 via a wired or wireless link. In embodiments that further include one or more EMG amplifiers external to the wrist box 306, the computer device 308 is also coupled to the EMG amplifier output(s). An example embodiment of the computer device 308 is discussed below in connection with FIG. 15. In an embodiment, the computer device 308 includes a DAQ unit to sample analog output signals received from the wrist box 306 and to convert the analog signals into a digital format directly useable by the computer device 308.

The computer device 308 processes the output signals from the sensors of the finger-mountable device 302 (subject to any analog processing of the wrist box 306 and conversion operations of the DAQ unit) according to one or more algorithms. For example, an algorithm may compare a change in pressure and/or voltage measurements (e.g., between a relaxed patient state and a simulated defecation patient state) to a set of one or more threshold values. Example methods and algorithms are discussed in more detail below in connection with FIGS. 11-13.

Based on the processing of the sensor output signals, the computer device 308 provides an indication of whether the sensor readings correspond to an anorectal disorder. For example, the computer device 308 may provide a binary indication of whether the sensor outputs correspond to a dyssynergic defecation condition, in an embodiment. As another example, the computer device 308 may provide a binary indication of whether the sensor outputs correspond to (a) an absence of dyssynergic defecation or (b) an indeterminate condition for which further testing is advisable, in an embodiment. As yet another example, the computer device 308 may provide a non-binary indicator (e.g., a continuous-value indicator) indicating a likelihood (e.g., percent chance) that a patient has a dyssynergic defecation condition, in an embodiment. In some embodiments, the computer device 308 instead (or additionally) provides one or more of the above indicators with respect to fecal incontinence. In an embodiment, the computer device provides the indication as output data that is stored in a persistent memory. In some embodiments, the computer device 308 provides the indication via a display of a graphical user interface (GUI), such as the GUI discussed below in connection with FIGS. 14A-14C. Other outputs according to various embodiments are discussed below in connection with FIG. 13.

According to various embodiments, the analog and digital processing of the controller assembly 304 may be distributed in a manner different than that discussed above in connection with FIG. 9. For example, the controller assembly 304 does not include a wrist box 306 in some embodiments (e.g., the analog processing of the wrist box 306 instead occurs in the computer device 308, in another device that is not secured to the physician, or via circuitry that is included in the finger-mountable device 302 itself). In some of these embodiments, the finger-mountable device 302 is directly coupled to the computer device 308 via a wired or wireless link. As another example, some but not all of the analog processing of the controller assembly 304 (e.g., one or more preamplifiers) is performed by circuitry included in the finger-mountable device 302 or another device. As another example, some or all of the analog and digital processing of the controller assembly 304 instead occurs within the housing of the wrist box 306, or instead occurs within the finger-mountable device 302 itself.

Figure 10:
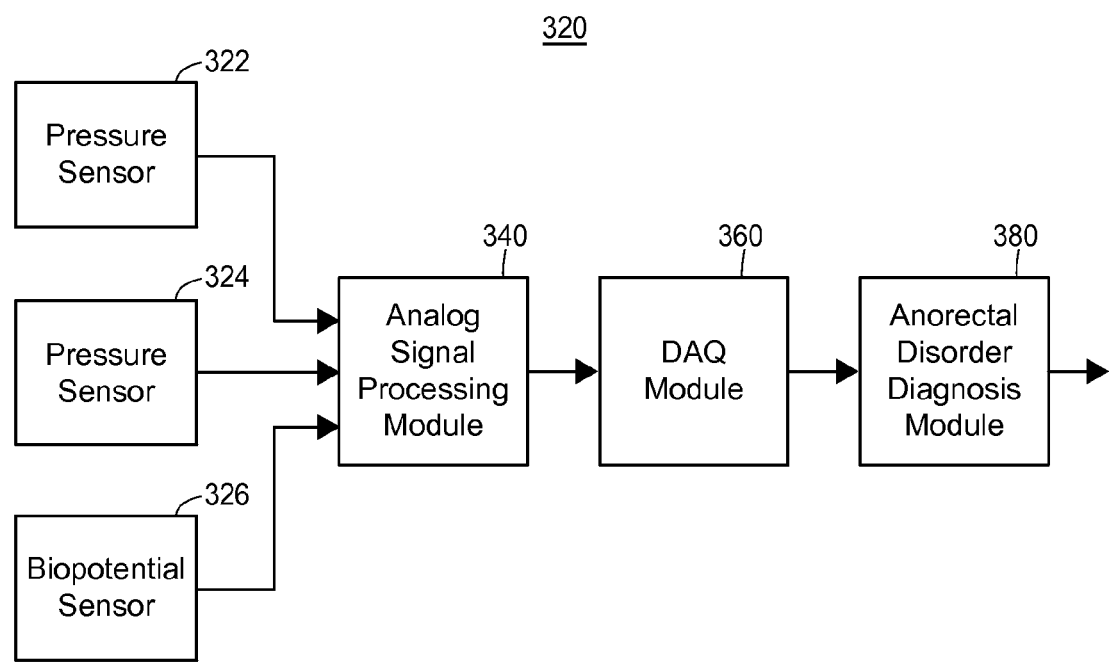
FIG. 10 is another block diagram of an example system for diagnosing an anorectal disorder.

FIG. 10 is another block diagram of an example system 320 for diagnosing an anorectal disorder. The system 320 includes a first pressure sensor 322, a second pressure sensor 324, and a biopotential sensor 326. According to various embodiments, each of the sensors 322, 324, and/or 326 may comprise multiple sensors. The pressure sensor 322 may be the anal sphincter pressure sensors 130A and 130B of FIG. 3B, the pressure sensor 324 may be the intrarectal pressure sensor 130C of FIG. 3B, and the biopotential sensor may be the puborectalis activity sensor 130D (e.g., EMG electrodes) of FIG. 3B, for example. In some embodiments, the system 320 does not include the sensor 322 and/or the sensor 326. In some embodiments, the system 320 includes additional sensors (e.g., an inertial sensor).

An analog signal processing module 340 is coupled to the output of each of the sensors 322, 324, and 326. The analog signal processing module 340 amplifies and/or filters the output signals of sensors 322, 324, and/or 326, in some embodiments. The analog signal processing module 340 may be similar to the wrist box 306 (and, in some embodiments, the external EMG amplifier(s)) discussed in connection with FIG. 9, for example.

A DAQ module 360 is coupled to the output of the analog signal processing module 340. The DAQ module 360 samples analog signals output by the analog signal processing module 340 and converts the analog signals into a digital format directly useable by a constipation diagnosis module 380, in an embodiment. The DAQ module 360 may include an analog-to-digital (DAC) converter, for example. In an embodiment, the DAQ module 360 has less than 200 ms delay and at least a 10 kS/s sample rate.

The anorectal disorder diagnosis module 380 is coupled to the output of the DAQ module 360. The anorectal disorder diagnosis module 380 includes at least one processor that analyzes the sensor output signals (as processed by analog signal processing module 340 and converted by DAQ module 360) according to one or more algorithms. The processor(s) of the diagnosis module 380 also causes one or more indicators relating to an anorectal disorder (e.g., dyssynergic defecation, fecal incontinence, etc.) diagnosis to be generated. The anorectal disorder diagnosis module 380 may be the computer device discussed above in connection with FIG. 9, for example.

In some embodiments, the system 320 does not include a separate analog signal processing module 340. For example, the functionality of the analog signal processing module 340 is distributed among one or more of sensors 322, 324, and 326, or is included in the DAQ unit 360, in some embodiments.

Figure 11:
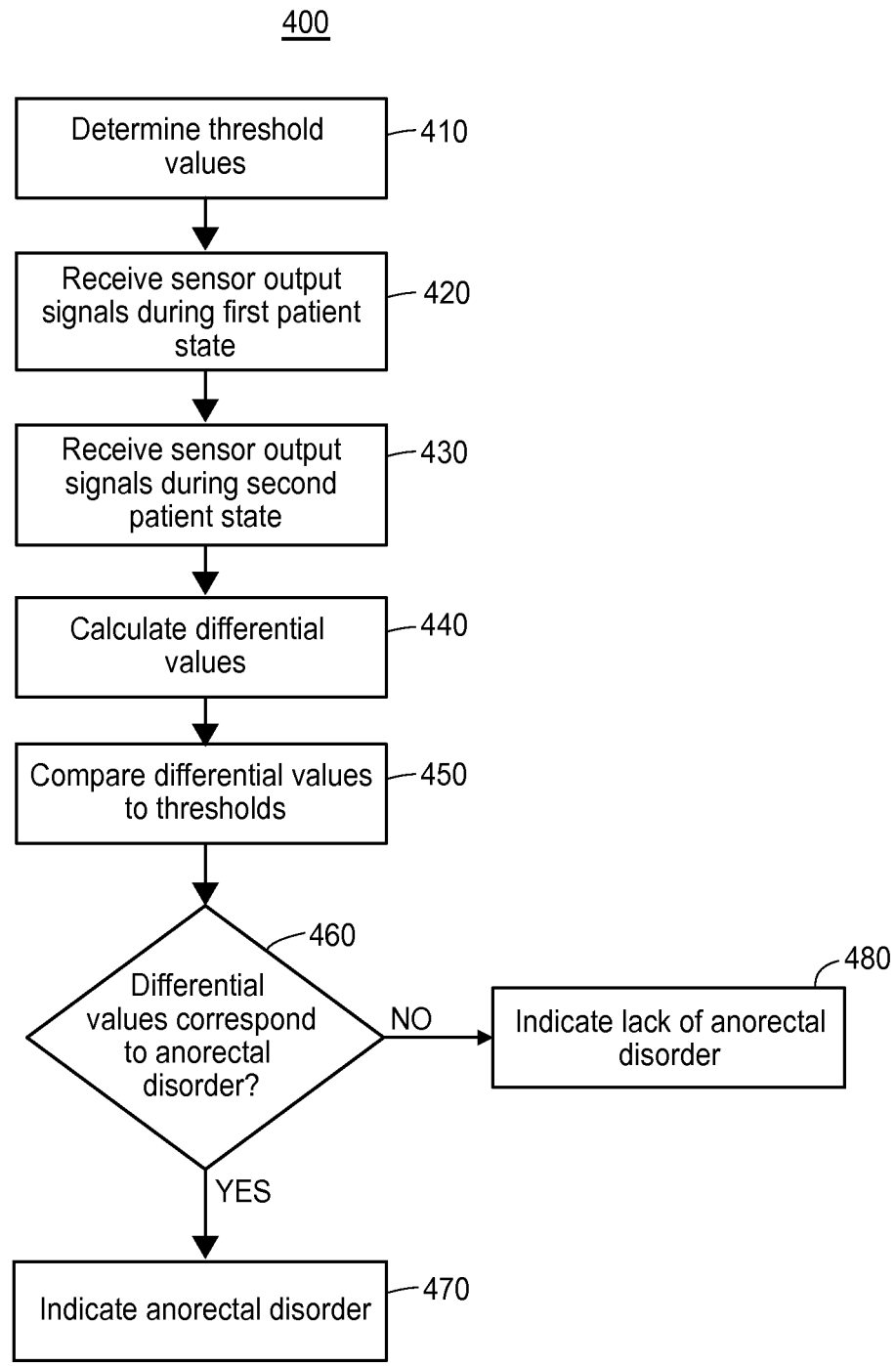
FIG. 11 is a flow diagram of an example method for diagnosing an anorectal disorder.

FIG. 11 is a flow diagram of an example method 400 for diagnosing an anorectal disorder. In an embodiment, the method 400 is performed by a computer device that is coupled (e.g., via a wrist box) to a finger-mountable sensor device. For example, the method 400 may be performed by the computer device 308 of FIG. 9 or the diagnosis module 380 of FIG. 10.

The method 400 may determine one or more threshold values (block 410). In an embodiment, the threshold values correspond to differences between two sensor measurement values at two different times, either in units (e.g., mmHg or μV) or as a percentage difference. In some embodiments, a set of one or more threshold values is determined for each type of sensor measurement. For example, one set of threshold values may correspond to measurements of one or more anal sphincter pressure sensors, one set of threshold values may correspond to measurements of one or more intrarectal pressure sensors, and one set of threshold values may correspond to measurements of one or more puborectalis activity sensors. In some embodiments, each type of sensor measurement is associated with a first threshold value relating to how much a measurement value increases and a second threshold value relating to how much a measurement value decreases. In embodiments that include one or more EMGs, the corresponding threshold values may be determined with respect to the actual detected voltage (e.g., in μV) or with respect to the voltage as amplified, etc., by any analog processing.

In some embodiments, some or all of the threshold values are determined by accessing a local or remote persistent memory (e.g., a database stored in a local hard drive or portable memory, or in a remote server). In some embodiments, some or all of the threshold values are determined by utilizing user interface hardware and software to determine threshold values manually entered by a user (e.g., via a GUI).

While a patient is in a first state (e.g., a baseline state), and while the sensors are properly positioned within the patient (e.g., the finger-mountable device of FIGS. 3A-3C or FIGS. 5 and 6 is inserted in the patient as shown in FIGS. 7A and 7B), sensor output signals may be received (block 420). In one embodiment, where the anorectal disorder being diagnosed is dyssynergic defecation, the first state is a relaxed state during which the patient is not making an effort to defecate. In another embodiment, where the anorectal disorder being diagnosed is fecal incontinence, the first state is a relaxed state during which the patient is not contracting the anal sphincter muscle. In an embodiment, sensor output signals are received from each of one or more anal sphincter pressure sensors, one or more intrarectal pressure sensors, and one or more puborectalis activity sensors (e.g., the sensors described above in connection with FIG. 3B). In some embodiments, the output signals are received via intermediate devices or modules, such as the analog signal processing module 340 and DAQ module 360 of FIG. 10.

While the patient is in a second state (e.g., a non-baseline state), and while the sensors remain properly positioned within the patient, additional sensor output signals may be received (block 430). In one embodiment, where the anorectal disorder being diagnosed is dyssynergic defecation, the second state is a simulated defecation state. In another embodiment, where the anorectal disorder being diagnosed is fecal incontinence, the second state is a state in which the patient contracts the anal sphincter muscle. The output signals corresponding to the second state of the patient may be received from the same sensors from which output signals are received at block 420, and may be received in the same manner as the output signals received at block 420 (e.g., via analog processing and/or DAQ modules), for example.

Based on the signals received at blocks 420 and 430, one or more differential values are calculated (block 440). The differential values may be calculated in a manner corresponding to the threshold values determined at block 410 (e.g., in terms of units such as mmHg or mV, or in terms of a percentage change). In an embodiment, each differential value is a difference between a measurement value corresponding to output signals for a particular type of sensor at two different times. For example, one of the differential values may be a difference between an anal sphincter pressure sensor measurement at a first time when the patient is in the first state, and a second time when the patient is in the second state. As another example, one of the differential values may be a difference between an intrarectal pressure sensor measurement at a first time when the patient is in the first state, and a second time when the patient is in the second state. As yet another example, one of the differential values may be a voltage difference between a puborectalis activity sensor (e.g., EMG) measurement at a first time when the patient is in the first state, and a second time when the patient is in the second state.

Once calculated, the differential values may be compared to the threshold values determined at block 410 (block 450). Differential values may be compared to the threshold values in different ways according to various embodiments. For example, some or all comparisons may comprise comparing the differential value to a signed (positive or negative) threshold value. As another example, some or all comparisons may comprise comparing the absolute value (magnitude) of the differential value to a threshold value. In embodiments where multiple threshold values were determined for a type of sensor (at block 410), the method 400 may compare the calculated differential value corresponding to that type of sensor to each of the multiple threshold values, or to only a particular threshold value corresponding to the sign of the differential value (e.g., to a threshold value corresponding to a decrease in value if the differential value is negative, and to a threshold value corresponding to an increase in value if the differential value is positive).

Based on the comparison at block 450, it is determined whether the differential values correspond to an anorectal disorder (block 460). In an embodiment, the anorectal disorder is dyssynergic defecation. In another embodiment, the anorectal disorder is fecal incontinence. In some embodiments, the determination at block 460 includes determining whether various calculated differential values are greater than or less than the corresponding threshold values. The determination at block 460 may be according to an algorithm such as the algorithm described below in connection with FIG. 13, for example. In some embodiments, one of various algorithms can be automatically selected based on a manual selection of the particular anorectal disorder being diagnosed.

If it is determined that the differential values correspond to the anorectal disorder at block 460, the anorectal disorder is indicated (block 470). If it is determined that the differential values do not correspond to the anorectal disorder at block 460, a lack of the anorectal disorder is indicated (block 480). The indication may take different forms according to various embodiments. For example, the indication may comprise output data generated by a processor, and/or a visually perceptible indicator (e.g., an indicator on a displayed GUI, such as the GUI discussed below in connection with FIGS. 114-14C). In an embodiment, the indication is a binary indication of whether the differential values (as compared to the threshold values) correspond to the anorectal disorder. In another embodiment, the indication is a binary indication of whether the differential values (as compared to the threshold values) correspond to (a) an absence of the anorectal disorder or (b) an indeterminate condition for which further testing is advisable. In yet another embodiment, the indication is a non-binary indicator (e.g., a continuous-value indicator) indicating a likelihood (e.g., a percent chance) that a patient has the anorectal disorder.

In other embodiments, certain steps of the method 400 may be omitted, repeated, or performed in an order different than that shown in FIG. 11. In some embodiments, for example, the threshold values determined at block 410 correspond to absolute measurement values (e.g., in mmHg or mV) rather than differential values. In these embodiments, one or both of blocks 420 and 440 may be omitted. As another example, block 430 may occur before block 420, and/or blocks 420, 430, and/or 440 may occur before block 410, in some embodiments. As yet another example, block 430 and the following blocks may repeat one or more times, in some embodiments. In one embodiment, for example, if a lack of an anorectal disorder is indicated (block 480), flow of the method 400 proceeds back to block 430 and a new set of one or more sensor output signals is received.

In some embodiments, additional steps may be included in the method 400. For example, the method 400 may include steps wherein some or all of the sensor output signals are received over a continuous time window, and wherein some or all of the signals are processed to determine the level of coordination between multiple muscle groups (e.g., anal sphincter muscle and puborectalis muscle), in some embodiments. In these embodiments, the determination at block 460 may additionally be based on whether the level of muscle coordination corresponds to an anorectal disorder (e.g., dyssynergic defecation). Coordination is discussed in more detail below in connection with FIG. 10A. As another example, the method 400 may include an additional step wherein sensor output signals are received while the patient is in a third state (e.g., a second non-baseline state, such as a state in which the patient is contracting the puborectalis and/or anal sphincter muscles).

Figure 12A:
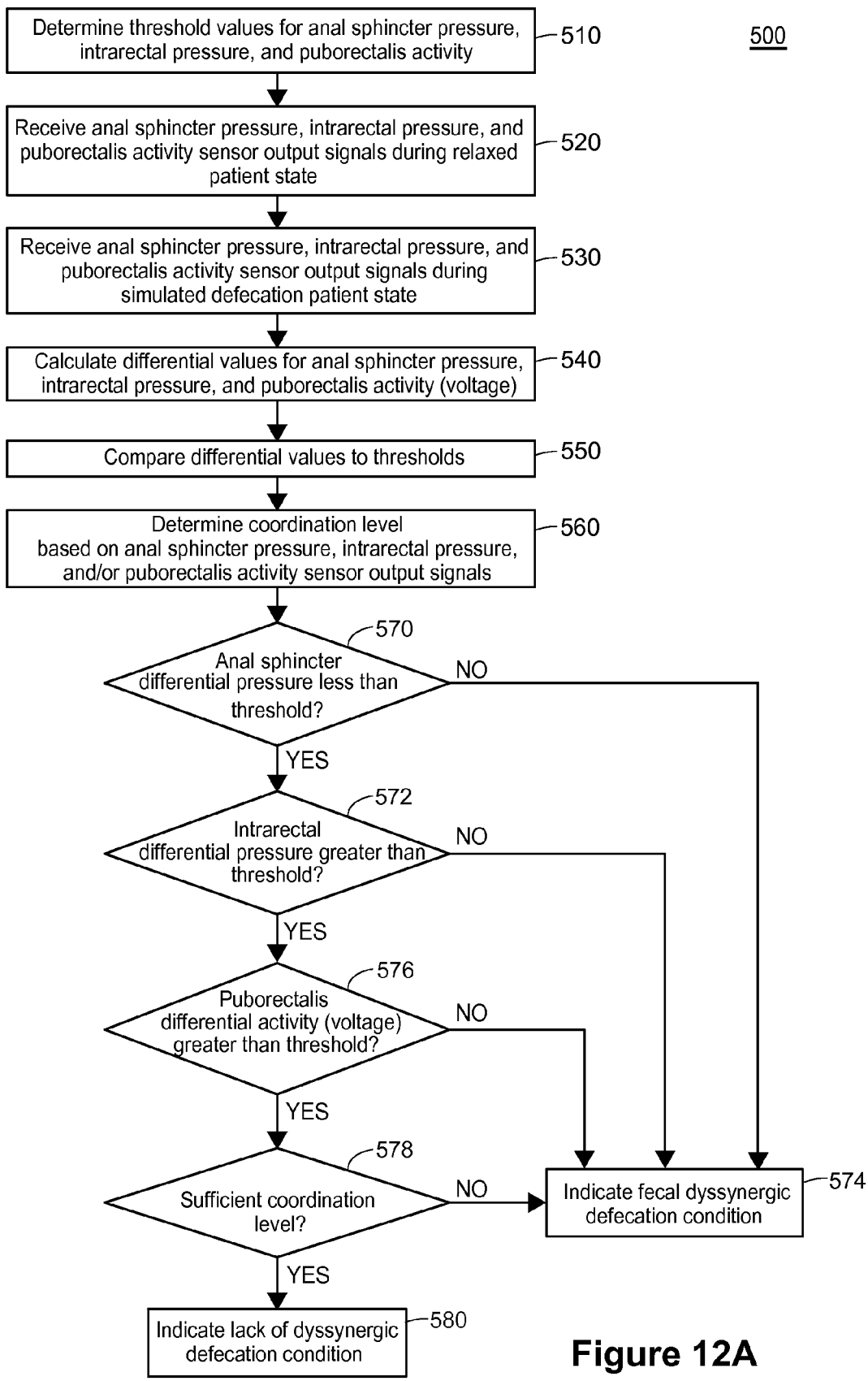
FIG. 12A is a flow diagram of an example method for diagnosing dyssynergic defecation.

FIG. 12A is a flow diagram of an example method 500 for diagnosing dyssynergic defecation. In an embodiment, the method 500 is performed by a computer device coupled (e.g., via a wrist box) to a finger-mountable sensor device. For example, the method 500 may be performed by the computer device 308 of FIG. 9 or the diagnosis module 380 of FIG. 10.

The method 500 may determine threshold values corresponding to anal sphincter pressure, intrarectal pressure, and intrarectal biopotential (block 510). In an embodiment, the threshold values correspond to differences between two sensor measurement values at two different times, either in units (e.g., mmHg or mV) or as a percentage difference. In some embodiments, a set of one or more threshold value is determined for each of the three types of sensor measurements (i.e., anal sphincter pressure, intrarectal pressure, and puborectalis activity). In some embodiments, each type of sensor measurement is associated with a first threshold value relating to how much a measurement value increases and a second threshold value relating to how much a measurement value decreases.

In some embodiments, some or all of the threshold values are determined by accessing a local or remote persistent memory (e.g., a database stored in a local hard drive or portable memory, or in a remote server). In some embodiments, some or all of the threshold values are determined by utilizing user interface hardware and software to determine threshold values manually entered by a user (e.g., via a GUI).

While a patient is in a relaxed state (e.g., not making an effort to defecate), and while the sensors are properly positioned within the patient (e.g., the finger-mountable device of FIGS. 3A-3C or FIGS. 5 and 6 is inserted in the patient as shown in FIGS. 7A and 7B), output signals may be received from the anal sphincter pressure sensor(s), intrarectal pressure sensor(s), and puborectalis activity sensor(s) (block 520). In some embodiments, the output signals are received via intermediate devices or modules, such as the analog signal processing module 340 and DAQ module 360 of FIG. 10.

While the patient is in a simulated defecation state, and while the sensors remain properly positioned within the patient, additional anal sphincter pressure, intrarectal pressure, and puborectalis activity sensor output signals may be received (block 530). The output signals may be received in the same manner (e.g., via analog processing and/or DAQ modules) as the output signals received at block 520, for example.

Based on the signals received at blocks 520 and 530, one or more differential values are calculated (block 540). The differential values may be calculated in a manner corresponding to the threshold values determined at block 510 (e.g., in terms of units such as mmHg for the anal sphincter and intrarectal pressure sensor signals and mV for the puborectalis activity sensor signals, or in terms of a percentage change). In an embodiment, each differential value is a difference between a measurement value corresponding to output signals for a particular type of sensor at two different times. For example, one of the differential values may be a difference between the anal sphincter pressure sensor measurement value at a first time when the patient is in a relaxed state, and a second time when the patient is in a simulated defecation state. As another example, one of the differential values may be a difference between the intrarectal pressure sensor measurement value at a first time when the patient is in a relaxed state, and a second time when the patient is in a simulated defecation state. As yet another example, one of the differential values may be a voltage difference between the puborectalis activity sensor (e.g., EMG) measurement at a first time when the patient is in a relaxed state, and a second time when the patient is in a simulated defecation state.

Once calculated, the differential values may be compared to the threshold values determined at block 510 (block 550). Differential values may be compared to the threshold values in different ways according to various embodiments, such as the embodiments discussed above in connection with block 450 of FIG. 11.

Based on output signals received from some or all of the three types of sensors, a coordination level of one or more pressures, EMG potentials, and/or other parameters is determined (block 560). "Coordination level" refers to a quantification of a volitional or involuntary characteristic sequence of events that can be observed in the time domain as a patient goes from one state to another state (e.g., from a relaxed state to a simulated defecation state). For example, a (simulated or actual) defecation, a cough, a sneeze, a Valsalva maneuver, and a Kegel maneuver are each expected to be accompanied by a particular sequence of events involving various muscles in the body. The characteristic sequence of events may be measured in terms of temporal relationships between one or more measured parameters (e.g., intrarectal pressure, anal sphincter pressure, puborectalis EMG activity, change in anorectal angle, EMG activity on the surface of the abdominal wall, etc.), and/or the amplitudes of the changes in the one or more measured parameters.

The coordination level may be quantified, in some embodiments, as a certain type or degree of latency of one signal with respect to another signal. In one embodiment, a coordination level reflects whether a first signal leads (or lags) a second signal. In another embodiment, a coordination level reflects whether a first signal leads (or lags) a second signal once the first and/or second signal has exceeded a positive or negative threshold that defines the bounds of an initial state. For example, a coordination level may reflect whether a first signal leads (or lags) a second signal once the first and/or second signal has deviated from an initial state by a threshold equal to two times a standard deviation of the signal(s).

In some embodiments, a coordination level reflects whether, or to what degree, a particular sequence of events involving one or more signal measurements has occurred. For example, a coordination level may be quantified by cross-correlating measured signals to analyze the magnitude of the proportional (or inversely proportional) relationships between the signals. In some embodiments, a coordination level reflects whether, or to what degree, agonism or antagonism exists between muscles. For example, increases in puborectalis EMG potential may be expected to accompany increases in anal sphincter pressure, in a healthy anorectal physiology. As another example, when a patient attempts to cough, the central nervous system is expected to increase anal sphincter muscle squeeze pressure and puborectalis EMG activity, prior to increasing diaphragm and abdominal wall EMG potential (in order to develop the cough), and prior to an increase in rectal pressure, in order to guard against involuntary loss of stool.

In an embodiment, the coordination level is determined by processing output signals from one or more of the anal sphincter pressure, intrarectal pressure, and/or puborectalis activity sensors over a particular time window (e.g., between the time that output signals are received at block 520 and the time that output signals are received at block 530).

Based on one of the comparisons at block 550, it is determined whether the differential value of the anal sphincter pressure is less than a corresponding threshold value determined at block 510 (block 570). If the differential value is less than (or, in some embodiments, less than or equal to) the corresponding threshold value, flow proceeds to block 572. If the differential value is greater than (or, in some embodiments, greater than or equal to) the corresponding threshold value, a dyssynergic defecation condition is indicated (block 574). In various embodiments, the indication may be similar to the indication of an anorectal disorder as described above in connection with block 470 of FIG. 11.

At block 572, it is determined whether the differential value of the intrarectal pressure is greater than a corresponding threshold value determined at block 510. If the differential value is greater than (or, in some embodiments, greater than or equal to) the corresponding threshold value, flow proceeds to block 576. If the differential value is less than (or, in some embodiments, less than or equal to) the corresponding threshold value, the dyssynergic defecation condition is indicated at block 574.

At block 576, it is determined whether the differential value of the puborectalis activity sensor voltage measurement is less than a corresponding threshold value determined at block 510. If the differential value is less than (or, in some embodiments, less than or equal to) the corresponding threshold value, flow proceeds to block 578. If the differential value is greater than (or, in some embodiments, greater than or equal to) the corresponding threshold value, the dyssynergic defecation condition is indicated at block 574.

At block 578, it is determined whether the coordination level determined at block 560 is sufficient. For example, the coordination level may be determined to be sufficient if the anal sphincter pressure, the intrarectal pressure, and/or the puborectalis EMG activity follow an expected sequence, as determined by meeting certain thresholds within certain time windows. If the coordination level is sufficient, a lack of a dyssynergic defecation condition is indicated (block 580). In various embodiments, the indication may be similar to the indication of a lack of an anorectal disorder as described above in connection with block 480 of FIG. 11. If the differential coordination level is not sufficient, the dyssynergic defecation condition is indicated at block 574.

In other embodiments, additional steps may be included in the method 500, and/or certain steps may be omitted, repeated, or performed in an order different than that shown in FIG. 12A. In some embodiments, for example, the threshold values determined at block 510 correspond to absolute measurement values (e.g., in mmHg or mV) rather than differential values. In these embodiments, one or both of blocks 520 and 540 may be omitted. As another example, block 530 may occur before block 520, and/or blocks 520, 530, and/or 540 may occur before block 510, in some embodiments. As yet another example, block 530 and the following blocks may repeat one or more times, in some embodiments. In one embodiment, for example, if a lack of a dyssynergic defecation condition is indicated (block 580), flow of the method 500 proceeds back to block 530 and a new set of one or more sensor output signals is received.

In some embodiments, blocks 570, 572, 576, and 578 may occur in a different order than that shown in FIG. 12A. Moreover, in some embodiments, the determinations at two, three, or all of blocks 570, 572, 576, and 578 occur regardless of the outcome of each determination. In some of these embodiments, the indications at blocks 574 and 580 may further comprise indications corresponding to the outcome of each of the individual determinations at blocks 570, 572, 576, and/or 578.

Figure 12B:
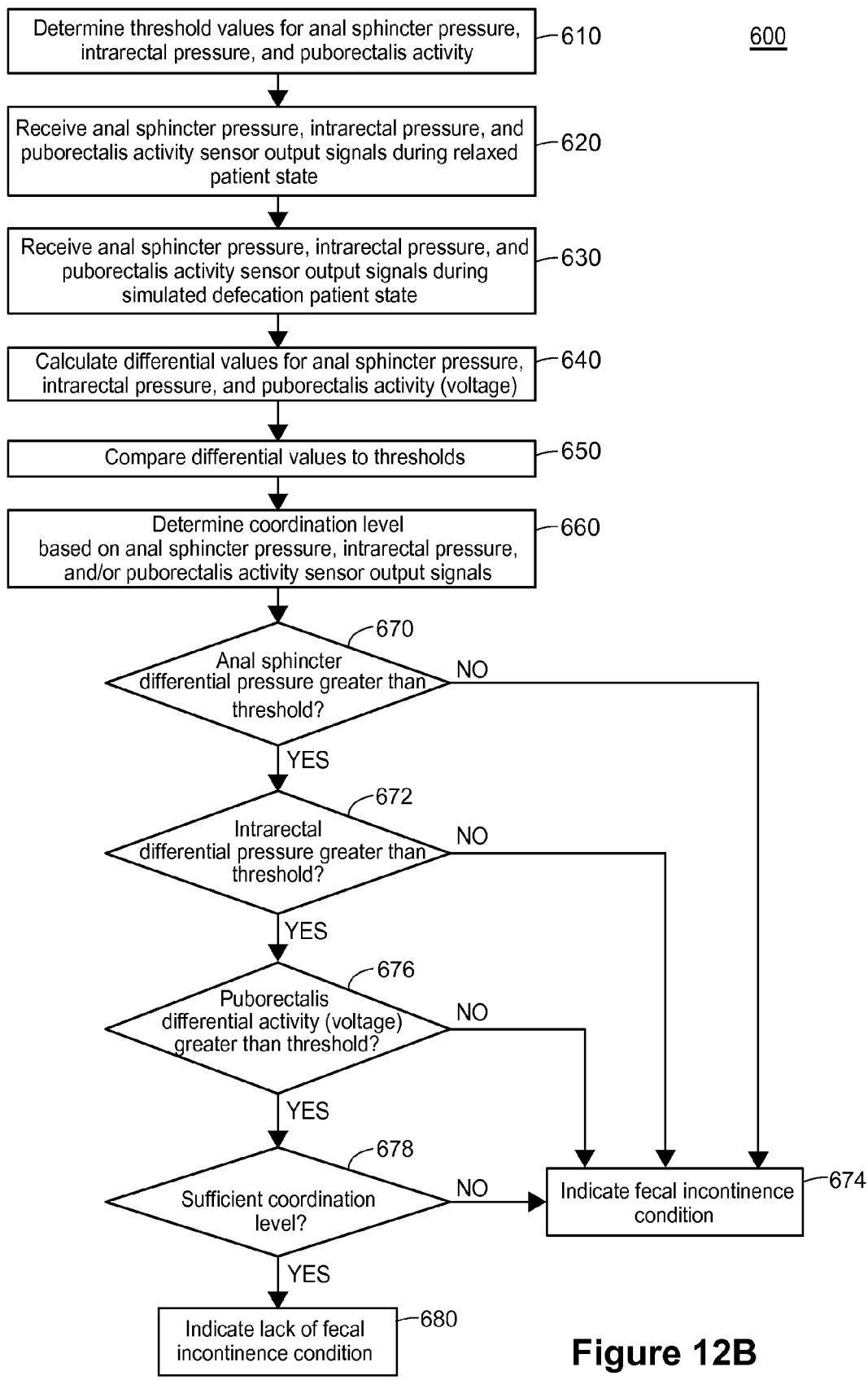
FIG. 12B is a flow diagram of an example method for diagnosing fecal incontinence.

FIG. 12B is a flow diagram of an example method 600 for diagnosing fecal incontinence. In an embodiment, the method 600 is performed by a computer device coupled (e.g., via a wrist box) to a finger-mountable sensor device. For example, the method 600 may be performed by the computer device 308 of FIG. 9 or the diagnosis module 380 of FIG. 10.

The method 600 may determine threshold values corresponding to anal sphincter pressure, intrarectal pressure, and intrarectal biopotential (block 610). Block 610 may be similar to block 510 of the method 500 illustrated in FIG. 12A, for example.

While a patient is in a relaxed state (i.e., not making an effort to contract the anal sphincter or pelvic floor muscles), and while the sensors are properly positioned within the patient (e.g., the finger-mountable device of FIGS. 3A-3C or FIGS. 5 and 6 is inserted in the patient as shown in FIGS.

7A and 7B), output signals may be received from the anal sphincter pressure sensor(s), intrarectal pressure sensor(s), and puborectalis activity sensor(s) (block 620). In some embodiments, the output signals are received via intermediate devices or modules, such as the analog signal processing module 340 and DAQ module 360 of FIG. 10.

While the patient is attempting to contract the anal sphincter and/or pelvic floor muscles, and while the sensors remain properly positioned within the patient, additional anal sphincter pressure, intrarectal pressure, and puborectalis activity sensor output signals may be received (block 630). The output signals may be received in the same manner (e.g., via analog processing and/or DAQ modules) as the output signals received at block 620, for example.

Based on the signals received at blocks 620 and 630, one or more differential values are calculated (block 640). The differential values may be calculated in a manner corresponding to the threshold values determined at block 610 (e.g., in terms of units such as mmHg for the anal sphincter and intrarectal pressure sensor signals and mV for the puborectalis activity sensor signals, or in terms of a percentage change). In an embodiment, each differential value is a difference between a measurement value corresponding to output signals for a particular type of sensor at two different times. For example, one of the differential values may be a difference between the anal sphincter pressure sensor measurement value at a first time when the patient is in a relaxed state, and a second time when the patient is attempting to contract the anal sphincter and/or pelvic floor muscles. As another example, one of the differential values may be a difference between the intrarectal pressure sensor measurement value at a first time when the patient is in a relaxed state, and a second time when the patient is attempting to contract the anal sphincter and/or pelvic floor muscles. As yet another example, one of the differential values may be a voltage difference between the puborectalis activity sensor (e.g., EMG) measurement at a first time when the patient is in a relaxed state, and a second time when the patient is attempting to contract the anal sphincter and/or pelvic floor muscles.

Once calculated, the differential values may be compared to the threshold values determined at block 610 (block 650). Differential values may be compared to the threshold values in different ways according to various embodiments, such as the embodiments discussed above in connection with block 450 of FIG. 11.

Based on output signals received from some or all of the three types of sensors, a coordination level of one or more pressures, EMG potentials, and/or other parameters is determined (block 660). Block 660 may be similar to block 560 of FIG. 12A, for example.

Based on one of the comparisons at block 650, it is determined whether the differential value of the anal sphincter pressure is greater than a corresponding threshold value determined at block 610 (block 670). If the differential value is greater than (or, in some embodiments, greater than or equal to) the corresponding threshold value, flow proceeds to block 672. If the differential value is less than (or, in some embodiments, less than or equal to) the corresponding threshold value, a fecal incontinence condition is indicated (block 674). In various embodiments, the indication may be similar to the indication of an anorectal disorder as described above in connection with block 470 of FIG. 11.

At block 672, it is determined whether the differential value of the intrarectal pressure is greater than a corresponding threshold value determined at block 610. If the differential value is greater than (or, in some embodiments, greater than or equal to) the corresponding threshold value, flow proceeds to block 676. If the differential value is less than (or, in some embodiments, less than or equal to) the corresponding threshold value, the fecal incontinence condition is indicated at block 674.

At block 676, it is determined whether the differential value of the puborectalis activity sensor voltage measurement is greater than a corresponding threshold value determined at block 610. If the differential value is greater than (or, in some embodiments, greater than or equal to) the corresponding threshold value, flow proceeds to block 678. If the differential value is less than (or, in some embodiments, less than or equal to) the corresponding threshold value, the fecal incontinence condition is indicated at block 674.

At block 678, it is determined whether the coordination level determined at block 660 is sufficient. For example, the coordination level may be determined to be sufficient if the anal sphincter pressure, the intrarectal pressure, and/or the puborectalis EMG activity follow an expected sequence, as determined by meeting certain thresholds within certain time windows. If the coordination level is sufficient, a lack of a fecal incontinence condition is indicated (block 680). In various embodiments, the indication may be similar to the indication of a lack of an anorectal disorder as described above in connection with block 480 of FIG. 11. If the differential coordination level is not sufficient, the fecal incontinence condition is indicated at block 674.

In other embodiments, additional steps may be included in the method 600, and/or certain steps may be omitted, repeated, or performed in an order different than that shown in FIG. 12B. In some embodiments, for example, the threshold values determined at block 610 correspond to absolute measurement values (e.g., in mmHg or mV) rather than differential values. In these embodiments, one or both of blocks 620 and 640 may be omitted. As another example, block 630 may occur before block 620, and/or blocks 620, 630, and/or 640 may occur before block 610, in some embodiments. As yet another example, block 630 and the following blocks may repeat one or more times, in some embodiments. In one embodiment, for example, if a lack of a fecal incontinence condition is indicated (block 680), flow of the method 600 proceeds back to block 630 and a new set of one or more sensor output signals is received.

In some embodiments, blocks 670, 672, 676, and 678 may occur in a different order than that shown in FIG. 12B. Moreover, in some embodiments, the determinations at two, three, or all of blocks 670, 672, 676, and 678 occur regardless of the outcome of each determination. In some of these embodiments, the indications at blocks 674 and 680 may further comprise indications corresponding to the outcome of each of the individual determinations at blocks 670, 672, 676, and/or 678.

Figure 13:
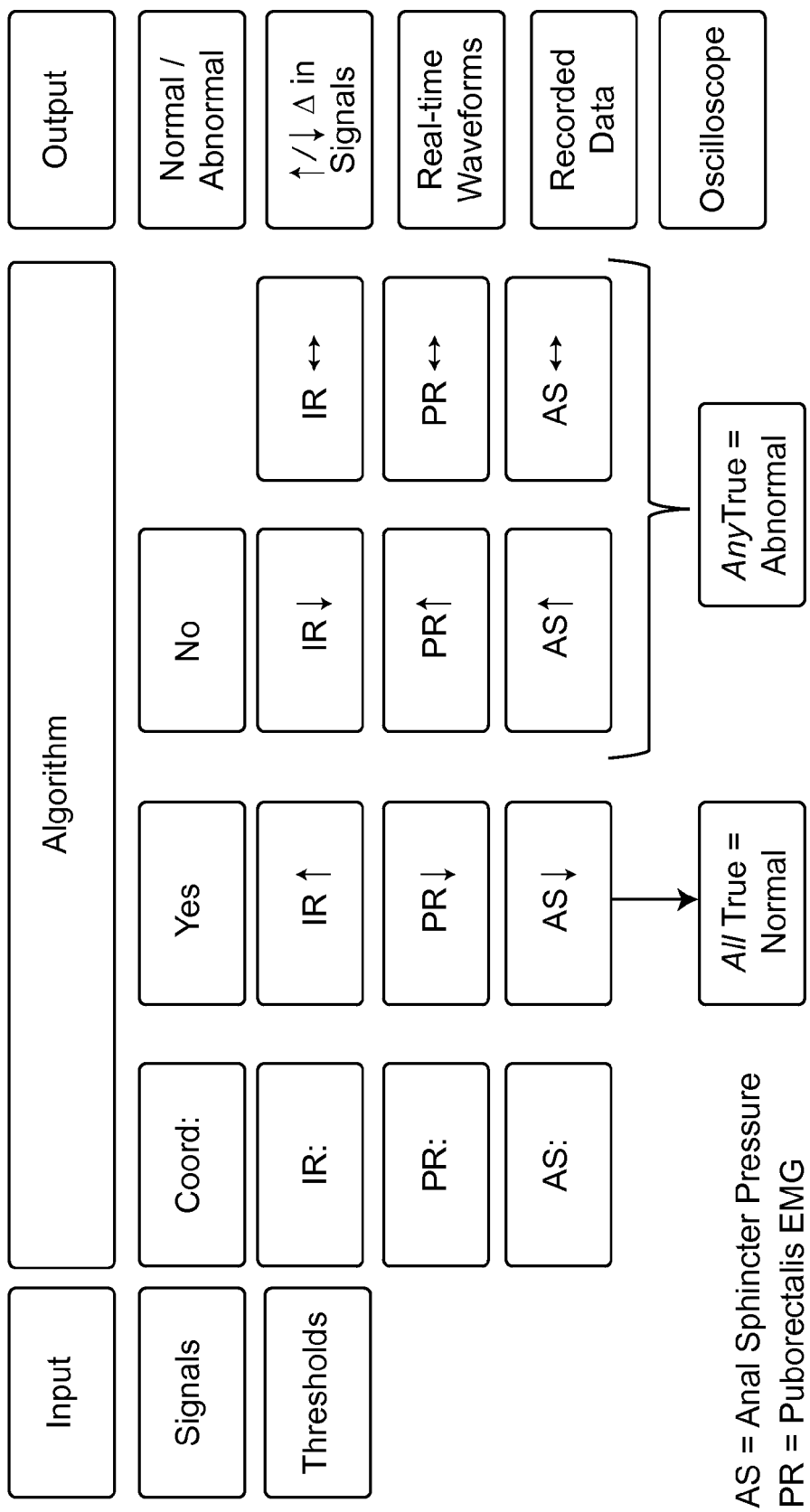
FIG. 13 is a diagram of an example algorithm utilized in a system for diagnosing dyssynergic defecation, such as the example system of FIG. 7 or FIG. 8, with example inputs and outputs of the system.

FIG. 13 is a diagram of an example algorithm utilized in a system for diagnosing dyssynergic defecation, such as the example system 300 of FIG. 9 or the example system 320 of FIG. 10, with example inputs and outputs of the system. In an embodiment, the algorithm is coded in a software application. The software application may be stored in a persistent memory such as a hard drive or portable memory, and may include instructions that can be executed by a processor of a computer device such as the computer device 308 of FIG. 9 or the anorectal disorder diagnosis module 380 of FIG. 10.

The example algorithm of FIG. 13 receives as inputs output signals from one or more anal sphincter pressure sensors, one or more intrarectal pressure sensors, and one or more puborectalis activity sensors. In an embodiment, one set of received signals corresponds to a relaxed state of the patient being diagnosed, and one set of received signals corresponds to a simulated defecation state of the patient being diagnosed. In some embodiments, the received signals correspond to a larger set of samples over a predetermined or manually adjustable time window that includes the relaxed and simulated defecation states of the patient.

The example algorithm also receives as inputs thresholds corresponding to each of the anal sphincter pressure sensor(s), intrarectal pressure sensor(s), and puborectalis activity sensor(s). The thresholds may be in terms of units (e.g., mmHg or mV) or percent change, for example. In an embodiment, the algorithm also receives as an input one or more thresholds corresponding to a coordination level. The threshold(s) may be in units or percent change, for example. In some embodiments, at least one of the thresholds corresponds to a maximum or minimum time window (e.g., a window in which a certain measurement should or should not exceed another received threshold).

The example algorithm determines a difference in value for each sensor measurement type (in the embodiment shown, anal sphincter pressure, intrarectal pressure, and puborectalis activity (voltage)) between a time at which the patient is in a relaxed state and a time at which the patient is in a simulated defecation state. The algorithm also determines a coordination level from some or all of the sensors (e.g., from the anal sphincter and intrarectal pressure sensors). The coordination level may be determined, for example, by processing the time-domain waveforms corresponding to anal sphincter pressure, intrarectal pressure, and/or puborectalis activity and determining whether the timing of anal sphincter and puborectalis muscle contractions corresponds to normal anorectal physiology.

Based on the determined differences and the level of coordination, the example algorithm determines whether various conditions are true or false. Specifically, the algorithm determines whether a sufficient coordination level exists, whether the intrarectal pressure has increased, whether the puborectalis activity (e.g., EMG voltage) has decreased, and whether the anal sphincter pressure has decreased. Each may be determined by comparing the respective measure with the corresponding threshold (e.g., the intrarectal pressure is determined to have "increased" only if the pressure increases by more than the corresponding threshold amount or percentage). In the case of coordination level, the algorithm may also determine whether one or more of the corresponding thresholds are exceeded within a corresponding threshold time window.

In an embodiment, a diagnostic output indicating normal anorectal physiology (e.g., indicating that dyssynergic defecation is not detected, or is not likely) is generated if all of these conditions are true, and an output indicating abnormal anorectal physiology (e.g., dyssynergic defecation is detected, or is likely) is generated if any condition is not true. In addition to this diagnostic output, the algorithm may in some embodiments generate outputs indicating whether each of the individual conditions was determined to be true or false. In an embodiment, another output includes time-domain waveforms (e.g., real-time waveforms) corresponding to each measured value. Each of the outputs may be information displayed to a user (e.g., via a GUI), data stored in a persistent memory, and/or data sent to another device (e.g., a printer, an oscilloscope, etc.).

In other embodiments, algorithms different than the algorithm shown in FIG. 13 may be used to diagnose dyssynergic defecation. For example, an algorithm for diagnosing dyssynergic defecation may not determine whether one or more of the conditions shown in FIG. 13 (e.g., coordination) are satisfied, and/or may determine whether additional conditions not shown are satisfied. Moreover, other algorithms may be used to diagnose anorectal disorders other than dyssynergic defecation. Algorithms for diagnosing anorectal disorders other than dyssynergic defecation may be similar to the algorithm shown in FIG. 13, but determine whether fewer conditions and/or additional conditions not shown in FIG. 13 are satisfied, reverse the directionality of certain up/down arrows corresponding to the "Yes" and "No" outcomes shown in FIG. 13, etc. For example, an algorithm similar to the algorithm of FIG. 13, but with reversed directionality of the up/down arrows corresponding to anal sphincter pressure and puborectalis EMG, may be used to diagnose fecal incontinence (e.g., such that either of a differential anal sphincter pressure below a first threshold or a differential puborectalis EMG voltage below a second threshold indicates fecal incontinence).

Figure 14A:
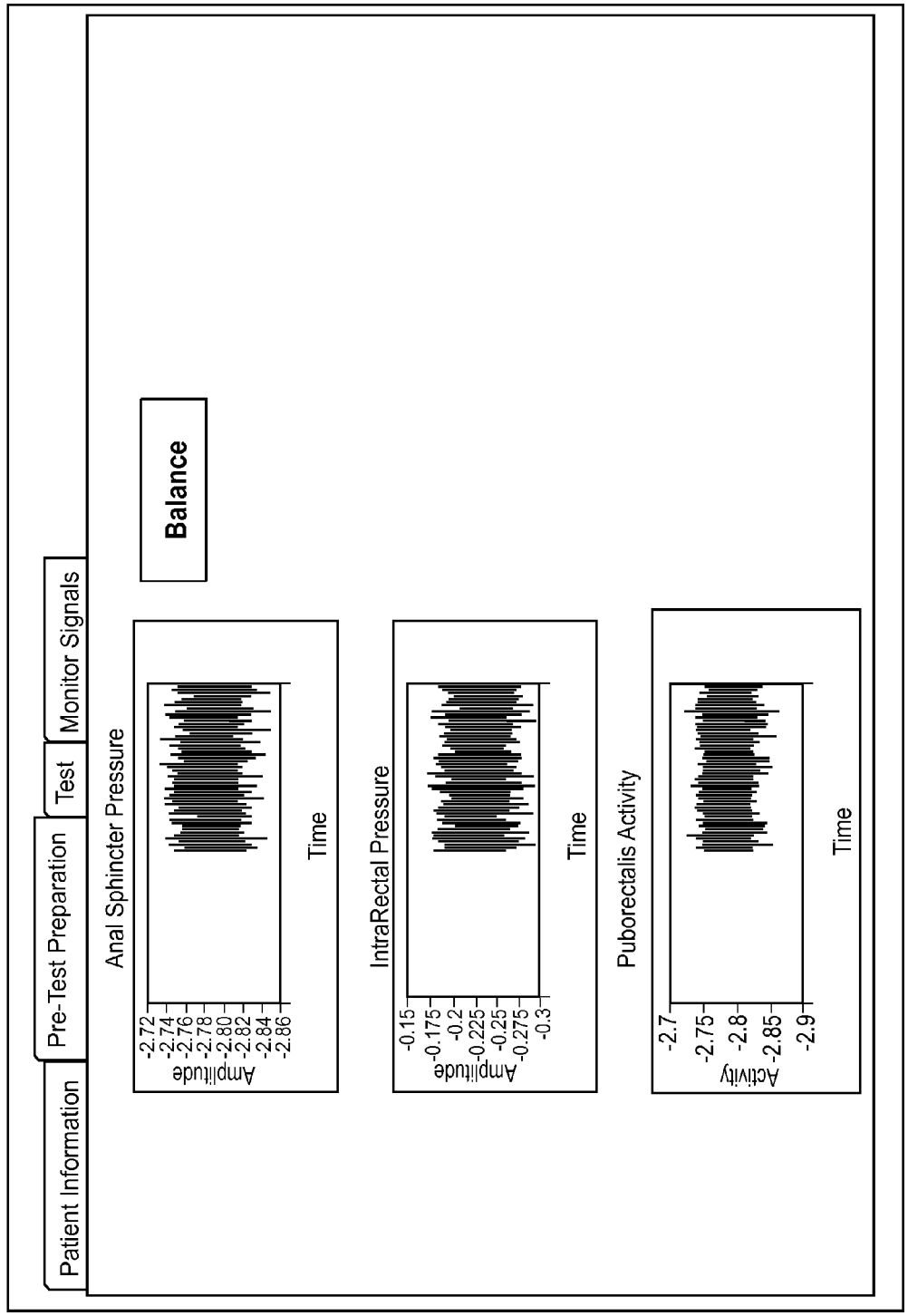
FIGS. 14A-14C are screen shots of a graphical user interface of an example software tool for diagnosing dyssynergic defecation.
Figure 14B:
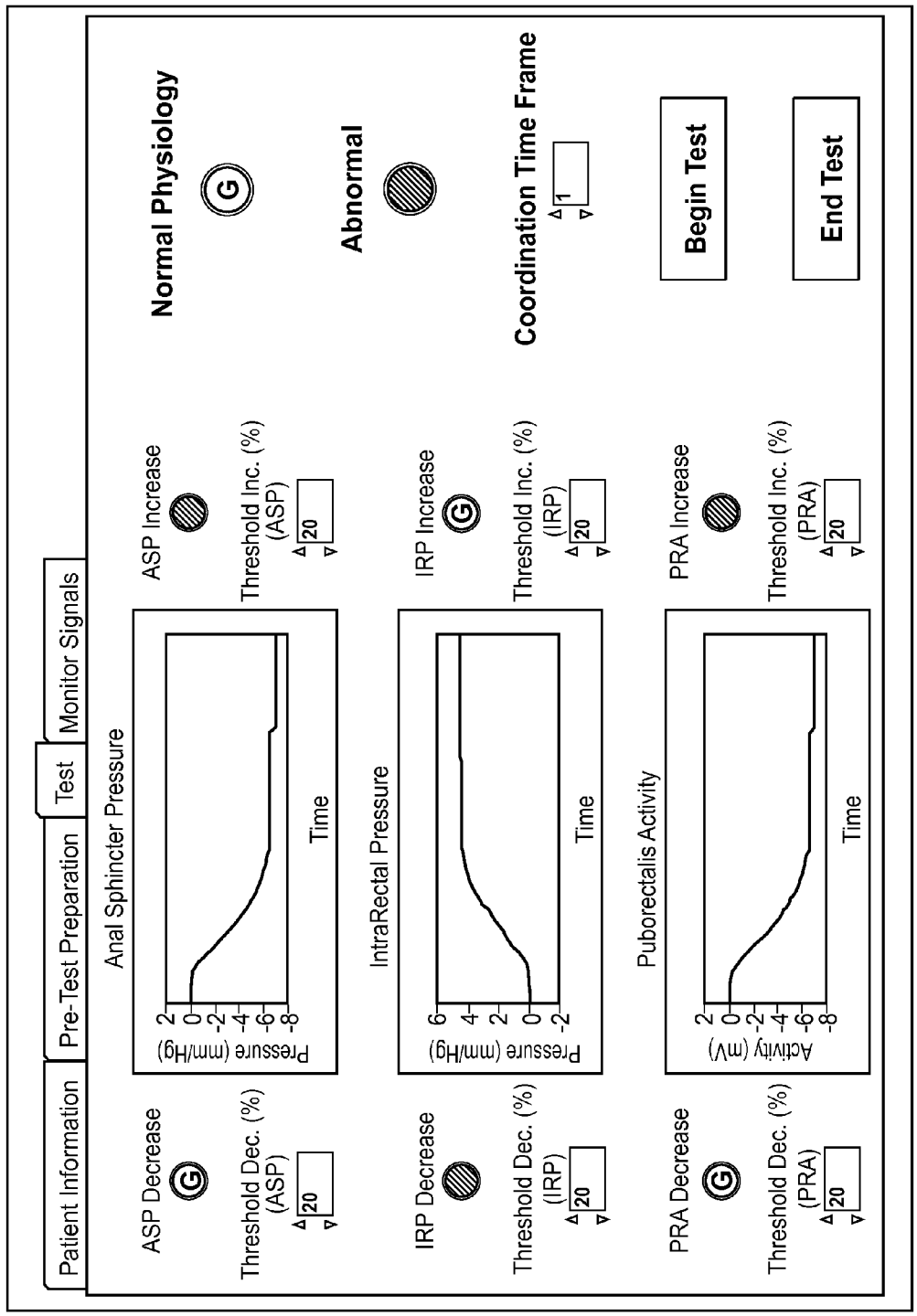
Figure 14C:
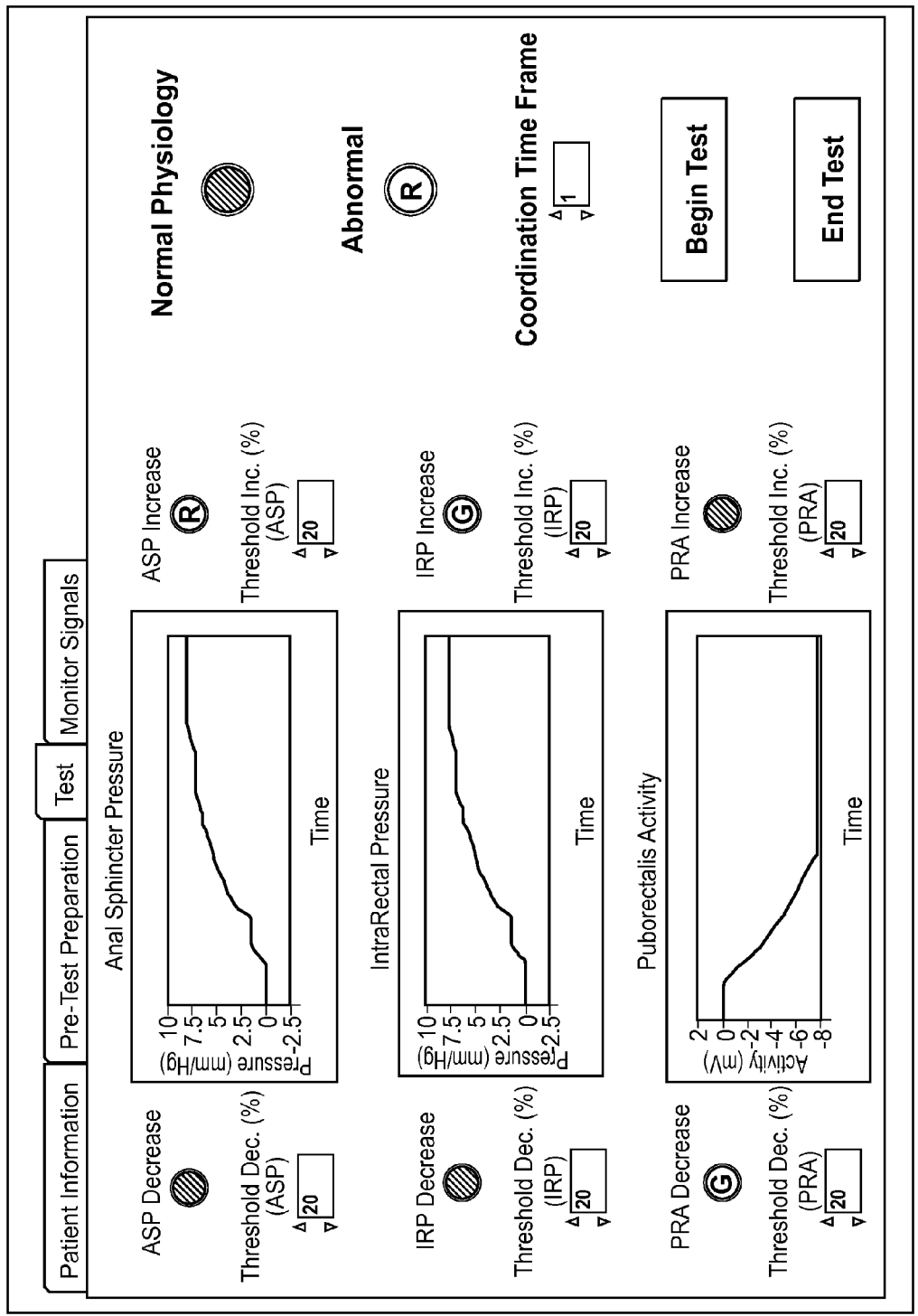

FIGS. 14A-14C are screen shots of a GUI of an example software tool for diagnosing dyssynergic defecation. The GUI may be generated by a software application including instructions that execute a method such as the method 400 of FIG. 11, for example. The GUI may be displayed on a display device (e.g., monitor, touch screen, etc.) of a computer device such as the computer device 308 of FIG. 9 or the anorectal disorder diagnosis module 380 of FIG. 10, for example.

Referring first to FIG. 14A, the GUI includes user-selectable tabs labeled "Patient Information", "Pre-Test Preparation", "Test", and "Monitor Signals". When the Patient Information tab is selected, the user may enter information about the patient under diagnosis, such as name, gender, weight, social security number, etc.

When the Pre-Test Preparation tab is selected, the user may gather baseline data for each type of sensor measurement (e.g., anal sphincter pressure, intrarectal pressure, puborecatlis activity) while the sensors (e.g., on a finger-mountable sensor device) are appropriately positioned within the patient and the patient is instructed to enter a relaxed state. To collect the baseline data, the user selects the "Balance" button depicted in FIG. 14A, in an embodiment. The GUI further displays a substantially real-time waveform for each type of sensor measurement, in an embodiment. In an embodiment, historical baseline data for a particular patient may be retrieved from a memory (e.g., a database of a remote server) rather than requiring a new baseline test.

When the Test tab is selected, the user may gather data for each type of sensor measurement while the sensors remain appropriately positioned within the patient and the patient is instructed to enter a simulated defecation state. Referring to FIG. 14B, the user may manually enter two percent-change thresholds for each type of sensor measurement, where a first threshold determines what degree of change corresponds to an "increase" in a measured value and a second threshold determines what degree of change corresponds to a "decrease" in a measured value. Once the thresholds are entered (or, in some embodiments, default values are left in place), the user may select the "Begin Test" button to begin recording data associated with the sensors, and "End Test" to stop recording the data. In an embodiment, the user instructs the patient to start attempting to defecate after the Begin Test button is selected, but before the End Test button is selected.

Based on differences between the data recorded while in the Pre-Test Preparation tab and data recorded while in the Test tab, and based on the entered or default threshold values, an algorithm determines whether the data corresponds to a normal or abnormal anorectal physiology, and the result is indicated to the user via the GUI. FIG. 14B illustrates an example GUI where a normal physiology (e.g., no dyssynergic defecation) is diagnosed, and FIG. 14C illustrates an example GUI where an abnormal physiology (e.g., dyssynergic defecation) is diagnosed. More specifically, FIG. 14C represents an example GUI of a system executing an algorithm similar to the algorithm of FIG. 13 (but without taking into account coordination level), where an abnormal physiology is indicated because the anal sphincter pressure increased when the patient was in a simulated defecation state. In the embodiment of FIGS. 14B and 14C, other outputs displayed on the GUI include substantially real-time waveforms of the sensor measurement values, indications of whether each type of sensor measurement "increased" or "decreased" according to the appropriate threshold, and indications of whether each type of sensor measurement individually corresponded to a normal or abnormal condition. In the screen shots of FIGS. 14B and 14C, for example, a "G" (green) display button indicates that the respective parameter is within a "normal" range, an "R" (red) display button indicates that the respective parameter is within an "abnormal" range, and a display button with no letter (i.e., a "blank" display button) indicates that the respective parameter is not applicable. For example, whether a decrease in the anal sphincter pressure is within a negative threshold range may not be applicable when the anal sphincter pressure has increased rather than decreased. In some embodiments, the GUI may display data corresponding to past baseline and/or simulated defecation testing for a particular patient, based on saved, historical data. In some embodiments, the GUI may display real-time data corresponding to two or more tests being performed at the same time.

In some embodiments, test results for a patient in a simulated defecation state may be compared to data recorded from past tests involving the patient. For example, results for a patient may be averaged over multiple tests (e.g., multiple simulated defecation states). In some of these embodiments, the indication of a normal or abnormal anorectal physiology may be based on an average or other statistic relating to the results of the multiple tests.

When the Monitor Signals tab is selected, the user may observe real-time signals corresponding to one or more sensor measurements. The real-time signal displays allow a physician to determine whether he or she has properly placed the finger-mounted probe device within the patient's rectum. For example, a display showing a real-time signal corresponding to a distal EMG measurement may serve to inform the physician when the EMG sensor is properly situated relative to the puborectalis.

While the GUI screen shots of FIGS. 14A-14C correspond to an example software tool used to diagnosing dyssynergic defecation, other software tools instead (or additionally) may be used to diagnose other anorectal disorders. For example, a software tool may allow a physician to select whether dyssynergic defecation or fecal incontinence is being diagnosed, and display signal waveforms and/or indicators, and apply a particular algorithm, corresponding to the selected anorectal disorder.

Figure 15:
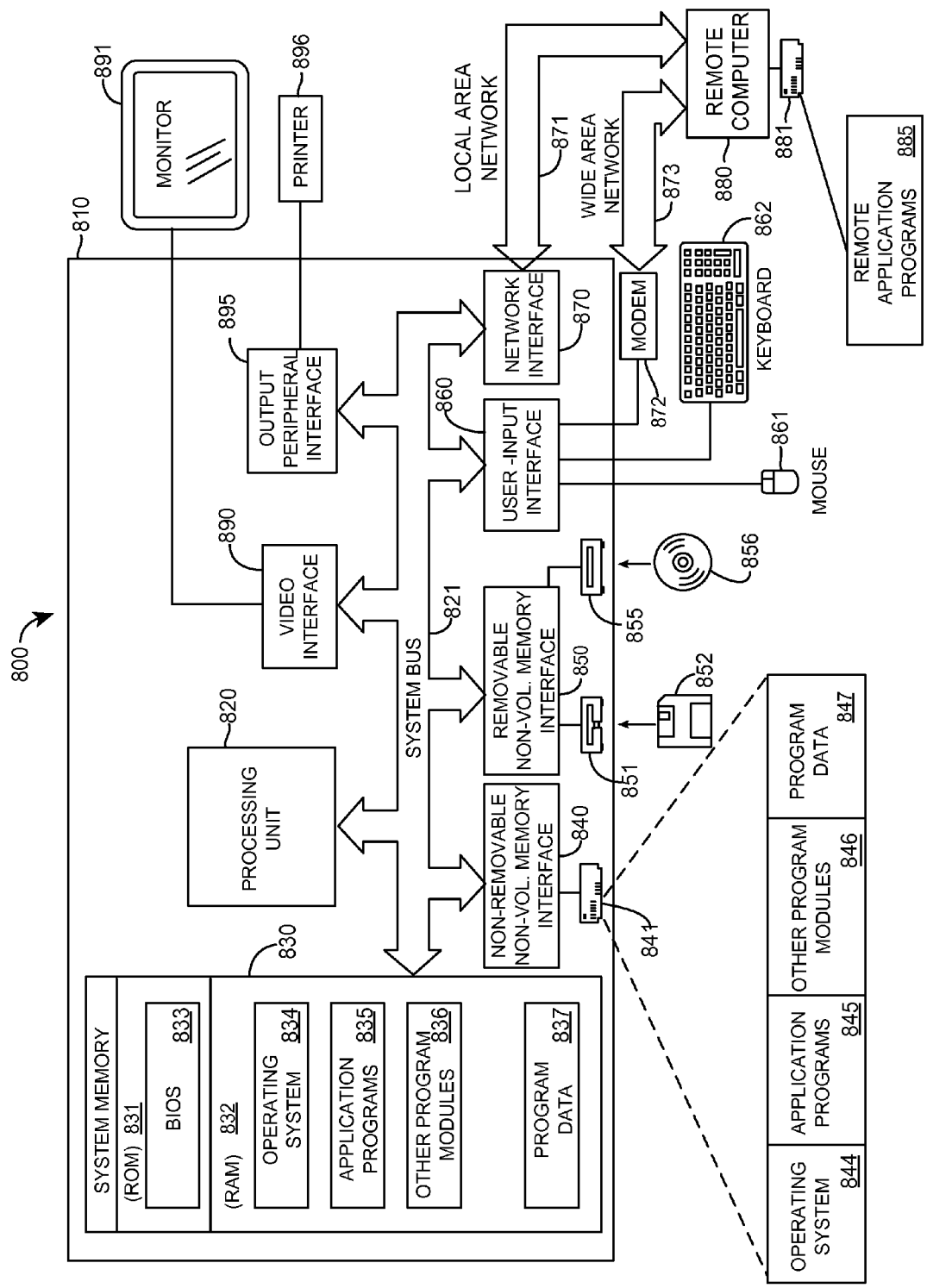
FIG. 15 is a block diagram of an example computer system on which a portion of a system for diagnosing an anorectal disorder may operate in accordance with the described embodiments.

FIG. 15 is a block diagram of an example computer system 800 on which a portion of a system for diagnosing an anorectal disorder may operate in accordance with the described embodiments. The computer system 800 of FIG. 15 includes a computing device in the form of a computer 810. The computer device 810 may be the computer device 308 of FIG. 9 or the anorectal disorder diagnosis module 380 of FIG. 10, for example. Components of the computer 810 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 810 typically includes a variety of computer readable media. Computer readable media can be any available media that can be accessed by computer 810 and includes both volatile and nonvolatile media, and both removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above are also included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 15 illustrates operating system 834, application programs 835, other program modules 836, and program data 837.

The computer 810 may also include other removable/non-removable, volatile/nonvolatile computer storage media. By way of example only, FIG. 15 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives and their associated computer storage media discussed above and illustrated in FIG. 15 provide storage of computer readable instructions, data structures, program modules and other data for the computer 810. In FIG. 15, for example, hard disk drive 841 is illustrated as storing operating system 844, application programs 845, other program modules 846, and program data 847. Note that these components can either be the same as or different from operating system 834, application programs 835, other program modules 836, and program data 837. Operating system 844, application programs 845, other program modules 846, and program data 847 are given different numbers here to illustrate that, at a minimum, they are different copies. A user may enter commands and information into the computer 810 through input devices such as a keyboard 862 and cursor control device 861, commonly referred to as a mouse, trackball or touch pad. A monitor 891 or other type of display device is also connected to the system bus 821 via an interface, such as a graphics controller 890. In addition to the monitor, computers may also include other peripheral output devices such as printer 896, which may be connected through an output peripheral interface 895.

The computer 810 may operate in a networked environment using logical connections to one or more remote computers, such as a remote computer 880. The remote computer 880 may be a personal computer, a server, a router, a network PC, a peer device or other common network node, and typically includes many or all of the elements described above relative to the computer 810, although only a memory storage device 881 has been illustrated in FIG. 15. The logical connections depicted in FIG. 15 include a local area network (LAN) 871 and a wide area network (WAN) 873, but may also include other networks. Such networking environments are commonplace in hospitals, offices, enterprise-wide computer networks, intranets and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the input interface 860, or other appropriate mechanism. In a networked environment, program modules depicted relative to the computer 810, or portions thereof, may be stored in the remote memory storage device 881. By way of example, and not limitation, FIG. 15 illustrates remote application programs 885 as residing on memory device 881. The communications connections 870, 872 allow the device to communicate with other devices. The communications connections 870, 872 are an example of communication media.

The methods of the anorectal disorder diagnosis embodiments described above may be implemented in part or in their entirety using one or more computer systems such as the computer system 800 illustrated in FIG. 15. The threshold values may be determined by a computer such as the computer 810. The threshold values may be received as a result of a user entering data through an input device such as the keyboard 862, for example. The sensor output signals (subsequent to analog processing, in some embodiments) may be received by computer such as the computer 810. The sensor output signals may be received via a DAQ unit (not shown in FIG. 15) internal or external to the computer 810, for example.

Some or all calculations performed in the anorectal disorder diagnosis embodiments described above (e.g., calculating differential values or comparing the differential values to threshold values) may be performed by a computer such as the computer 810, and more specifically may be performed by a processor such as the processing unit 820, for example. In some embodiments, some calculations may be performed by a first computer such as the computer 810 while other calculations may be performed by one or more other computers such as the remote computer 880. The calculations may be performed according to instructions that are part of a program such as the application programs 835, the application programs 845 and/or the remote application programs 885, for example.

Indicating an anorectal disorder (or lack thereof), as described above in the anorectal disorder diagnosis embodiments, may also be performed by a computer such as the computer 810. The indications may be made by setting the value of a data field stored in the ROM memory 831 and/or the RAM memory 832, for example. In some embodiments, indicating an anorectal disorder (or lack thereof) may include sending data over a network such as the local area network 871 or the wide area network 873 to another computer, such as the remote computer 881. In other embodiments, indicating an anorectal disorder (or lack thereof) may include sending data over a video interface such as the video interface 890 to display information relating to the anorectal disorder on an output device such as the monitor 891 or the printer 896, for example.

We claim:
1. A probe system comprising:
 a finger-mountable housing having a distal end and a proximal receptacle end, wherein the proximal receptacle end defines an opening to receive a finger; and
 a probe assembly, disposed on or within the finger-mountable housing and having at least (i) a puborectalis activity sensor to measure activity of a puborectalis muscle of a patient when the finger-mountable housing and probe assembly are inserted into an anus and rectum of the patient, (ii) a sphincter activity sensor to measure activity of an anal sphincter muscle of the patient when the finger-mountable housing and probe assembly are inserted into the anus and rectum of the patient, and (iii) an intrarectal pressure sensor to measure intrarectal pressure when the finger-mountable housing and probe assembly are inserted into the anus and rectum of the patient,
 wherein the puborectalis activity sensor includes at least a first electrode pair having a first conductive trace, strip, or wire and a second conductive trace, strip, or wire,
 wherein the first conductive trace, strip, or wire and the second conductive trace, strip, or wire (i) are each arranged to extend in a direction parallel to a longitudinal axis of the finger when the finger is inserted in the opening, and over at least a portion of a fingertip pad of the inserted finger, and (ii) are arranged with a spacing, relative to each other and in a direction perpendicular to the longitudinal axis of the inserted finger, that is between 2 mm and 8 mm,
 wherein the sphincter activity sensor includes at least a second electrode pair positioned at the proximal receptacle end of the finger-mountable housing, and wherein the intrarectal pressure sensor is positioned at the distal end of the finger-mountable housing, such that the intrarectal pressure sensor is adjacent a fingernail of the finger when the finger is inserted in the opening.

2. The probe system of claim 1, wherein the distal end of the finger-mountable housing has a tactile region for providing a sense of touch for the finger.

3. The probe system of claim 2, wherein the tactile region is an opening in the finger-mountable housing.

4. The probe system of claim 1, wherein the puborectalis activity sensor comprises two pairs of electrodes arranged in a double differential configuration.

5. The probe system of claim 1, wherein the probe assembly further comprises an inertial sensor configured to measure at least one selected from the group consisting of (i) acceleration of a tissue of the patient and (ii) velocity of the tissue.

6. The probe system of claim 1, wherein the probe assembly further comprises an anal sphincter pressure sensor located at the proximal receptacle end of the finger-mountable housing.

7. The probe system of claim 1, wherein the probe assembly further comprises a pH sensor.

8. The probe system of claim 1, wherein the probe assembly further comprises an osmolality sensor.

9. The probe system of claim 1, wherein the probe assembly further comprises an ultrasound transducer for ultrasound elastography.

10. The probe system of claim 1, wherein the probe assembly further comprises one or more sensors configured to measure a deformation of the finger-mountable housing.

11. The probe system of claim 1, wherein the probe assembly further comprises a plurality of pressure sensors of a sensor array having a generally spiral or concentric ring arrangement along at least a portion of a length between the distal end and the proximal receptacle end of the finger-mountable housing.

12. The probe system of claim 11, wherein the plurality of pressure sensors includes at least 40 pressure sensors arranged to provide a topographic pressure map.

13. The probe system of claim 1, wherein the probe assembly further comprises an adjustable-length pressure sensor.

14. The probe system of claim 1, further comprising a controller assembly communicatively coupled to the probe assembly.

15. The probe system of claim 14, wherein the controller assembly is configured to:
   determine a first differential value between a first and a second measurement of the puborectalis activity sensor,
   determine a second differential value between a first and a second measurement of the sphincter activity sensor,
   determine a third differential value between a first and a second measurement of the intrarectal pressure sensor, and
   provide an indication relating to a likelihood of an anorectal disorder based at least in part on the first, second, and third differential values.

16. The probe system of claim 15, wherein the anorectal disorder is dyssynergic defecation.

17. The probe system of claim 15, wherein the anorectal disorder is fecal incontinence.

18. The probe system of claim 14, wherein the controller assembly comprises a controller assembly housing and a processor.

19. The probe system of claim 18, wherein the controller assembly further comprises:
   an attachment mechanism mounted to the controller assembly housing and configured to be removably attachable to a user of the probe system; and
   a first plug receptacle for coupling the probe assembly to one or more circuits within the controller assembly housing via one or more wires.

20. The probe system of claim 19, wherein the controller assembly further includes a second plug receptacle for coupling the one or more circuits within the controller assembly housing to one or more circuits within a remote controller assembly housing, and wherein the one or more circuits within the remote controller assembly housing include the processor.

21. The probe system of claim 20, wherein the one or more circuits within the remote controller assembly housing are components of a remote personal computer, and wherein the one or more circuits within the controller assembly housing include an amplifier.

22. The probe system of claim 19, wherein the controller assembly further comprises a wireless transmitter for wirelessly coupling the one or more circuits within the controller assembly housing to the one or more circuits within the remote controller assembly housing.

23. The probe system of claim 1, wherein the probe assembly further comprises a first anal sphincter pressure sensor, a second anal sphincter pressure sensor, and a third anal sphincter pressure sensor radially spaced around a circumference of the proximal receptacle end of the finger-mountable housing.

24. The probe system of claim 1, wherein the finger-mountable housing is a multilayer structure comprising:
   an inner support layer maintaining structural integrity of the finger-mountable housing while the finger-mountable housing is inserted into the anus and rectum of the patient;
   a probe layer disposed adjacent to the inner support layer; and
   a flexible outer layer disposed to sandwich the probe layer between the inner support layer and the flexible outer layer.

25. The probe system of claim 24, wherein the probe layer includes a flex circuit having electrical leads for connecting the probe assembly to a controller assembly through an electrical receptacle.

26. The probe system of claim 24, wherein the probe layer includes an embedded wireless transmitter for wirelessly communicating with a controller assembly.

27. The probe system of claim 1, wherein the probe system comprises a glove, and wherein an index finger of the glove includes the finger-mountable housing.

28. The probe system of claim 1, wherein the first conductive trace, strip, or wire and the second conductive trace, strip, or wire are each arranged to extend over at least 6.5 mm of the fingertip pad in the direction parallel to the longitudinal axis of the inserted finger.

29. The probe system of claim 28, wherein the first conductive trace, strip, or wire and the second conductive trace, strip, or wire each have a width or diameter, in the direction perpendicular to the longitudinal axis of the inserted finger, that is 1.85 mm or less.

* * * * *

UNITED STATES PATENT AND TRADEMARK OFFICE
CERTIFICATE OF CORRECTION

PATENT NO. : 9,743,857 B2  
APPLICATION NO. : 13/714728  
DATED : August 29, 2017  
INVENTOR(S) : William D. Chey et al.

Page 1 of 1

It is certified that error appears in the above-identified patent and that said Letters Patent is hereby corrected as shown below:

On the Title Page

Item [72], Lines 3-4, "Los Angeles (CA)" should be -- Los Angeles, CA (US) --.

Signed and Sealed this  
Twentieth Day of February, 2018

Andrei Iancu  
*Director of the United States Patent and Trademark Office*